(12) United States Patent
Mansour et al.

(10) Patent No.: US 6,228,860 B1
(45) Date of Patent: *May 8, 2001

(54) SUBSTITUTED 1,3-OXATHIOLANES WITH ANTIVIRAL PROPERTIES

(75) Inventors: Tarek S. Mansour; Haolun Jin, both of Montreal (CA)

(73) Assignee: Biochem Pharma Inc., Laval (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/718,555

(22) PCT Filed: Apr. 19, 1995

(86) PCT No.: PCT/CA95/00212

§ 371 Date: Nov. 26, 1996

§ 102(e) Date: Nov. 26, 1996

(87) PCT Pub. No.: WO95/29176

PCT Pub. Date: Nov. 2, 1995

Related U.S. Application Data

(63) Continuation-in-part of application No. 08/230,317, filed on Apr. 20, 1994, now Pat. No. 5,587,480, which is a continuation-in-part of application No. 07/791,441, filed on Nov. 13, 1991, now abandoned, which is a continuation-in-part of application No. 07/612,840, filed on Nov. 13, 1990, now abandoned.

(51) Int. Cl.[7] .................. A61P 31/18; A61K 31/4718; C07D 411/04

(52) U.S. Cl. ..................... 514/262; 514/274; 544/317

(58) Field of Search ............... 544/317; 514/274, 514/262

(56) References Cited

U.S. PATENT DOCUMENTS

| | | | |
|---|---|---|---|
| 4,000,137 | 12/1976 | Dvonch et al. | 544/277 |
| 4,336,381 | 6/1982 | Nagata et al. | 544/313 |
| 5,039,667 | 8/1991 | Tyrrell et al. | 514/45 |
| 5,047,407 | 9/1991 | Belleau et al. | 514/274 |
| 5,118,672 | 6/1992 | Schinazi et al. | 514/47 |
| 5,159,067 | 10/1992 | Schinazi et al. | 536/27 |
| 5,587,480 | * 12/1996 | Belleau et al. | 544/310 |
| 5,703,058 | * 12/1997 | Schinazi et al. | 514/45 |

FOREIGN PATENT DOCUMENTS

| | | |
|---|---|---|
| 212 409 | 3/1987 | (EP) . |
| 337 713 | 10/1989 | (EP) . |
| 349 242 | 1/1990 | (EP) . |
| 363 582 | 4/1990 | (EP) . |
| 382 526 | 8/1990 | (EP) . |
| 2 063 257 | 6/1981 | (GB) . |
| 2 230 266 | 10/1990 | (GB) . |
| WO 88/08001 | 10/1988 | (WO) . |
| WO 89/04662 | 6/1989 | (WO) . |
| WO 90/12023 | 10/1990 | (WO) . |
| WO 91/01326 | 2/1991 | (WO) . |
| 92/08717 | * 5/1992 | (WO) . |

OTHER PUBLICATIONS

Hayden, F.G. *Goodman & Gilman's The Pharmacological Basis of Therapeutics*, ed. by Hardman, J.G. et al. (McGraw–Hill, New York), pp. 1191–1217 (1996).*
March, J. *Advanced Organic Chemistry*, (Wiley & Sons, New York), pp. 94–127 (1992).*
Coates, J.A.V. et al. *Antimicrobial Agents and Chemotherapy*, vol. 36, pp. 202–205 (1992).*
Daniels, T.C. et al. *Textbook of Organic Medicinal and Pharmaceutical Chemistry*, ed. by Wilson, C.O. et al. (Lippincott Company, Philadelphia), pp. 31–43 (1977).*
Mansour et al, J. Med. Chem., 38, 1995, 1–4.*
Baba, M. et al., "Both 2',3'–Dideoxythymidine and Its 2',3'–Unsaturated Derivative (2',3'–Dideoxythymidinene) Are Potent and Selective Inhibitors of Human Immunodificiency Virus Replication in Vitro," *Biochemical and Biophysical Research Communications*, 142, 1, pp. 128–134 (1987).
Balzarini, J. et al., "Potent and Selective Anti–HTLV–III/LAV Activity of 2',3'–Dideoxycytidinene, the 2',3'–Unsaturated Derivative of 2',3'–Dideoxycytidine," *Biochemical and Biophysical Research Communications*, 140, 2, pp. 735–742 (1986).
Belleau, B. et al., "Design and Activity of a Novel Class of Nucleoside Analogs Effective Against HIV–1," *Fifth International Conference on AIDS*, p. 515, Abstract T.C.O.1 (1989).
Belleau, B. et al., "A Novel Class of 1,3–Oxathiolane Nucleoside Analogues Having Potent Anti–HIV Activvity," *Bioorganic & Medicinal Chemistry Letters*, 3, 8, pp. 1723–1728 (1993).

(List continued on next page.)

*Primary Examiner*—John M. Ford
*Assistant Examiner*—Thomas McKenzie
(74) *Attorney, Agent, or Firm*—Millen, White, Zelano & Branigan, P.C.

(57) ABSTRACT

This invention relates to single enantiomers of novel cis-substituted 1,3-oxathiolanes, of the formula (I):

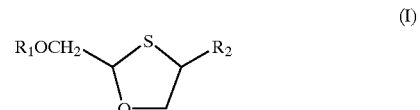

wherein;

$R_1$ is hydrogen, and $R_2$ is cytosine or 5-fluorocytosine, and pharmaceutically acceptable salts and esters thereof. This invention also relates to pharmaceutical compositions containing them and to the use of these compounds as antiviral agents, particularly in combination therapy.

20 Claims, No Drawings

OTHER PUBLICATIONS

Belleau, B. et al., "A Novel Class of 1,3–Oxathiolane Nucleoside Analogs Having Potent Anti–HIV Activity," *Chemical Abstracts*, 120, 15, p. 1101, Abstract 192195h (1994).

Cameron, J.M. et al., "Lamivudine," *Drugs of the Future*, 18, 4, pp. 319–323 (1993).

Carlisle, R. et al., "Cellular Pharmacology of the Anti–HIV Agent BCH–189 (2'–Deoxy–3'–Thiacytidine) in Human Peripheral Blood Mononuclear Cells (PBMC)," *American Association for Cancer Research Proceedings*, 31, p. 410, Abstract 2435 (1990).

Cassinelli, A. et al., "β–Haloalkylamine Derivatives with 1,3–Oxathiolane or 1,3–Dioxolane Nuclei," *European Journal of Medicinal Chemistry*, 22, pp. 5–10 (1987).

Deslongchamps, P., *Stereoelectronic Effects in Organic Chemistry*, pp. 24–27 (Pergamon Press Ltd., New York 1983).

Gosselin, G. et al., "Systematic Synthesis and Biological Evaluation of α– and β–D–Lyxofuranosyl Nucleosides of the Five Naturally Occurring Nucleic Acid Bases," *Journal of Medicinal Chemistry*, 30, pp. 982–991 (1987).

Grant, R. and Grant, C., *Grant & Hackh's Chemical Dictionary*, p. 53 (McGraw–Hill Book Co., 5th ed.) 1965.

Herdewijn, P. et al., "3'–Substituted 2',3'–Dideoxynucleoside Analogues as Potential Anti–HIV (HTLV–III/LAV) Agents," *Journal of Medicinal Chemistry*, 30, pp. 1270–1278 (1987).

House, H.O., *Modern Synthetic Reactions*, pp. 726–727 (Benjamin/Cummings Publishing Co., 2d ed.) 1973.

Huryn, D.M. et al., "Synthesis of Iso–ddA, Member of a Novel Class of Anti–HIV Agents," *Tetrahedron Letters*, 30, 46, pp. 6259–6262 (1989).

Huryn, D.M. et al., "Synthesis of Iso–ddA, Member of a Novel Class of Anti–HIV Agents: Dioxolane–T, a New 2',3'–Dideoxynucleoside Prototype with in Vitro Activity against HIV," *Chemtracts—Organic Chemistry*, 3, pp. 249–251 (1990).

Jones, M.F. et al., "Enantispecific Synthesis of 3'–Hetero–Dideoxy Nucleoside Analogues as Potential Anti–HIV Agents," *Journal of the Chemical Society, Perkin Transactions*, 1, pp. 1427–1436 (1992).

Lin, T. et al., "Synthesis and Antiviral Activity of Various 3'–Azido, 3'–Amino, 2',3'–Unsaturated, and 2',3'–Dideoxy Analogues of Pyrimidine Deoxyribonucleosides against Retroviruses," *Journal of Medicinal Chemistry*, 30, 2, pp. 440–444 (1987).

Mansour, T.S. et al., "Anti–Human Immunodeficiency Virus and Anti–Hepatitis–B Virus Activities and Toxicities of the Enantiomers of 2'–Deoxy–3'–Oxa–4'–Thiocytidine and Their 5–Fluoro Analogues in Vitro," *Journal of Medicinal Chemistry*, 38, 1, pp. 1–4 (1995).

Mansuri, M.M. et al., "Preparation of the Geometric Isomers of DDC, DDA, D4C and D4T as Potential Anti–HIV Agents," *Bioorganic & Medicinal Chemistry Letters*, 1, 1, pp. 65–68 (1991).

Mitsuya, H. et al., "3'–Azido–3'–Deoxythymidine (BW A509U): An Antiviral Agent that Inhibits the Infectivity and Cytopathic Effect of Human T–Lymphotropic Virus Type III/Lymphadenopathy–Associated Virus in Vitro," *Proc. Natl. Acad. Sci. USA*, 82, pp. 7096–7100 (1985).

Mitsuya, H. and Broder, S., "Inhibition of the in Vitro Infectivity and Cytopathic Effect of Human T–Lymphotropic Virus Type III/Lymphadenopathy–Associated Virus (HTLV–III/LAV) by 2',3'–Dideoxynucleosides," *Proc. Natl. Acad. Sci. USA*, 83, pp. 1911–1915 (1986).

Mitsuya, H. et al., "Rapid in Vitro Systems for Assessing Activity of Agents against HTLV–III/LAV," *AIDS: Modern Concepts and Therapeutic Challenges*, Chapter 18, pp. 303–333 (Samuel Broder, ed. 1987).

Morrison, R.T. and Boyd, R.N., *Organic Chemistry*, p. 1173 (Allyn and Bacon, Inc., 3d ed.).

Norbeck, D.W. et al., "(±)–Dioxolane–T ((±)–1–[(2β, 4β)–2–(Hydroxymethyl)–4–Dioxolanyl]Thymine), *Tetrahedron Letters*, 30, 46, pp. 6263–6266 (1989).

Romanelli, M.N. et al., "Enantioselectivity of Muscarinic Antagonists. 2,2–Dicyclohexyl–5–[(Dimethylamino)Methyl]–1,3–Oxathiolane Methiodides and Related 3–Oxides," *Journal of Medicinal Chemistry*, 31, 9, pp. 1698–1702 (1988).

Streitwieser, Jr., A. and Heathcock, C.H., *Introduction to Organic Chemistry*, pp. 188, 757, (Macmillan Publishing Co., New York, 3d ed. 1985).

Teodori, E. et al., "Resolution, Absolute Configuration, and Cholinergic Enantioselectivity of (–)– and (+)–c–2–Methyl–2–5–[(Dimethylamino)Methyl]–1,3–Oxathiolane t–3–Oxide Methiodide and Related Sulfones," *Journal of Medicinal Chemistry*, 30, 10, pp. 1934–1938 (1987).

Van Roey, P. et al., "Correlation between Preferred Sugar Ring Conformation and Activity of Nucleoside Analogues against Human Immunodeficiency Virus," *Proc. Natl. Acad. Sci. USA*, 86, pp. 3929–3933 (1989).

Wade, Jr., L.G., *Organic Chemistry*, pp. 252, 644, 684 (Prentice–Hall, Inc., New Jersey 1987).

Wainberg, M.A. et al., "Anti–HIV–1 Activity, Toxicity and Pharmacokinetics of Totally Novel Nucleoside Analogs," *Fifth International Conference on AIDS*, p. 552, Abstract M.C.P.63 (1989).

Wainberg, M.A. et al., "Characterization of AZT–Resistant Isolates of HIV–1: Susceptibility to Deoxythiacytidine and Other Nucleosides," *Sixth International Conference on AIDS*, 3, p. 117, Abstract S.B.87 (1990).

Wang, W. et al., "Synthesis of Optically Active 2',3'–Dideoxy–3'–Oxa–4'–Thio–Ribonucleoside Analogues by Transposition of a Leaving Group on Chiral Oxathiolanes via a Reductive–Oxidative Process," *Tetrahedron Letters*, 35, 27, pp. 4739–4742 (1994).

* cited by examiner

SUBSTITUTED 1,3-OXATHIOLANES WITH ANTIVIRAL PROPERTIES

This application is a national phase application under 35 U.S.C. Å371 of international application PCT /CA95/00212, filed Apr. 19, 1995, which in turn is a Continuation-in-Part of United States patent application Ser. No. 08/230/317, filed Apr. 20, 1994, now U.S. Pat. No. 5,587,480, which is a continuation in part of application Ser. No. 07/791,441, now abandoned, which is a continuation in part of application Ser. No. 07/612,840, now abandoned.

The present invention relates to novel substituted 1,3-oxathiolane compounds having pharmacological activity, to pharmaceutical compositions containing them, and to the use of these compounds in the antiviral treatment of mammals.

Retroviral infections are a serious cause of disease, most notably, the acquired immunodeficiency syndrome (AIDS*. The human immunodeficiency virus (HIV) has been recognized as the etiologic agent of AIDS.

Compounds having an inhibitory effect on HIV multiplication or otherwise effective in the therapy of retroviral infections are being actively sought.

H. Mitsuya et al., "3'-Azido-3'-deoxythymidine (BW A509U): An antiviral agent that inhibits the infectivity and cytopathic effect of human T-lymphotropic virus type III/lymphadenopathy-associated virus in vitro", *Proc. Natl. Acad. Sci. USA*, 82, pp. 7096–7100 (1985), refers to 3'-azido-3'-deoxythymidine of formula (A), commonly referred to as AZT. This compound is said to be useful in providing some protection for AIDS carriers against the cytopathogenic effect of immunodeficiency virus (HIV).

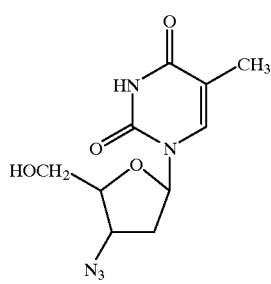

(A)

H. Mitsuya and S. Broder, "Inhibition of the in vitro infectivity and cytopathic effect of human T-lymphotrophic virus type III/lymphadenopathy-associated virus (HTLV-III/LAV) by 2',3'-dideoxynucleosides", *Proc. Natl. Acad. Sci. USA*, 83, pp. 1911–15 (1986), have also referred to a group of 2',3'-dideoxynucleosides shown in formula (B) which are said to possess protective activity against HIV-induced cytopathogenicity.

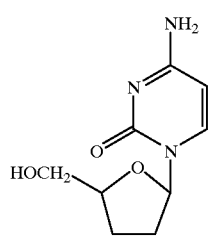

(B)

P. Herdewijn et al., "3'-Substituted 2',3'-dideoxynucleoside analogues as potential anti-HIV(HTLV-III/LAV) agents", *J. Med. Chem.*, 30, pp. 1270–1278 (1987), describe the anti-HIV activity of a series of 3'-substituted nucleoside analogues. While 3'-fluoro analogues of 3'-deoxythymidine and 2',3'-dideoxy-cytidine shown in formulas (C) and (D) are found to possess potent antiretroviral activity, substituents linked to the 3'-carbon via a thio or oxygen bridge did not yield active products.

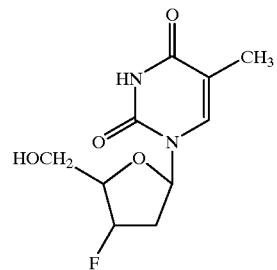

(C)

(D)

Analysis of molecular conformation studies in P. Van Roey et al., "Correlation between preferred sugar ring conformation and activity of nucleoside analogues against human immunodeficiency virus", *Proc. Natl. Acad. Sci. USA*, 86(10), pp. 3929–3933 (1989), indicate that active anti-HIV nucleoside analogues have 3' carbon conformations on the side opposite to the base.

D. Huryn et al., "Synthesis of iso-ddA, member of a novel class of anti-HIV agents", *Tetrahedron Lett.*, 30(46), pp. 6259–6262 (1989), refer to the iso-nucleoside analogue of formula (E) as a stable inhibitor of HIV replication.

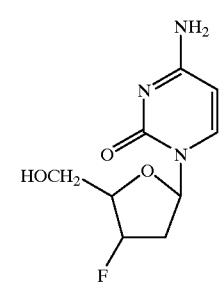

(E)

R. Vince and M. Hua, "Synthesis and anti-HIV activity of carbocyclic 2',3'-didehydro-2',3'-dideoxy 2,6-disubstituted purine nucleosides", *J. Med. Chem.*, 33(1), pp. 17–21 (1990), describe the analogues shown in formulas (F) and (G) as having anti-HIV activity. The unsaturated analogue (F) shows greater selectivity and potency as an inhibitor of HIV replication than the saturated analog (G).

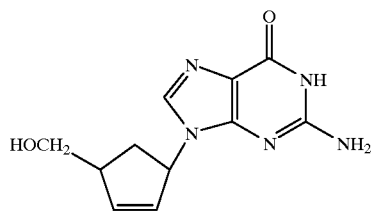

(F)

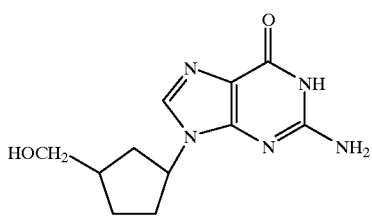

(G)

C. Chu et al., "Synthesis and structure-activity relationships of 6-substituted 2',3'-dideoxypurine nucleosides as potential anti-human immunodeficiency virus agents", *J. Med. Chem.*, 33(6), pp. 1553–1561 (1990), describe the $N_6$-methyl derivative shown in formula (H) as having greater potency against HIV than unmethylated 2',3'-dideoxyadenosine.

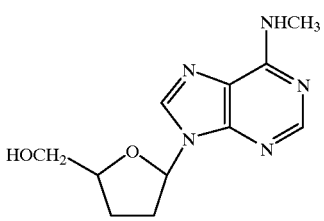

(H)

Finally, B. Belleau et al., "Design and activity of a novel class of nucleoside analogues effective against HIV-1", Abstracts of papers, Fifth International Conference on AIDS, Montreal, T.C.O. 1, p. 515 (1989), refer to dioxolanes and oxathiolanes of formulas (J) and (K) as having potent anti-HIV activity.

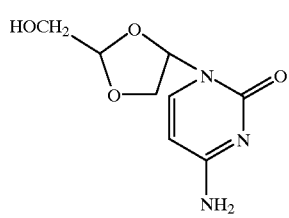

(J)

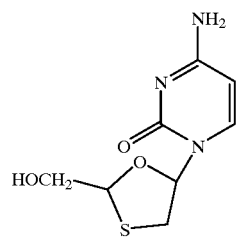

(K)

The cis isomer of formula (K) has been found to be active against HIV and HBV, and its unnatural enantiomer ((2R,5S cis) referred to as "the (-) enantiomer" has been found to have surprisingly low toxicity. Now named lamivudine or "3TC™", this new anti-viral drug is becoming the treatment of choice for combination therapy of AIDS patients and for sole therapy for HBV patients.

Although lamivudine (3TC™) has been found to be an extremely interesting compound in the clinic, there is always the possibility that the patient develops virus strains that are resistant to it after prolonged periods of treatment. There is therefore, still a need to develop anti-viral agents that are active against nucleoside-resistant viral strains, in particular, against 3TC™-resistant viral strains.

SUMMARY OF THE INVENTION

Classes of compounds known as 2-substituted 4-substituted 1,3-oxathiolanes have been found to have potent antiviral activity. In particular, these compounds have been found to act as potent inhibitors of HIV-1 replication in T-lymphocytes over a prolonged period of time with less cytotoxic side effects than compounds known in the art. These compounds have also been found active against 3TC-resistant HIV strains. These compounds are also useful in prophylaxis and treatment of hepatitis B virus infections.

There are accordingly provided in a first aspect of this invention a single enantiomer of compounds of formula (I) in the cis configuration:

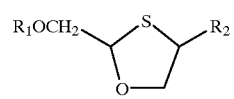

(I)

wherein $R_1$ is hydrogen, $R_2$ is cytosine or 5-fluorocytosine, and pharmaceutically acceptable salts and esters thereof.

As used herein, "a pharmaceutically acceptable salt, ester, or salt of such ester, of a compound of formula (I) or any other compound which, upon administration to the recipient, is capable of providing (directly or indirectly) a compound of formula (I) or an antivirally active metabolite or residue thereof.

Pharmaceutically acceptable salts of the compounds of formula (I) include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicylic, succinic, p-toluene sulfonic, tartaric, acetic, citric, methanesulfonic, formic, benzoic, malonic, naphthalene-2-sulfonic and benzenesulfonic acids. Other acids such as oxalic, while not in themselves pharmaceutically acceptable, may be useful in the preparation of salts useful as intermediates in obtaining the compounds of the invention and their pharmaceutically acceptable acid addition salts.

Salts derived from appropriate bases include alkali metal (e.g., sodium), alkaline earth metal (e.g., magnesium), ammonium and $N\text{-}(C_{1-4}\text{ alkyl})_4^+$ salts.

It will be appreciated by those skilled in the art that the compounds of formula (I) may be modified to provide pharmaceutically acceptable salts and esters thereof, at functional groups in both the cytosine moiety, and at the hydroxymethyl group of the oxathiolane ring, respectively. Modification at all such functional groups is included within the scope of the invention. However, of particular interest are pharmaceutically acceptable salts and esters (e.g., esters or esters of amino acids) obtained by modification of the 2-hydroxymethyl group of the oxathiolane ring.

Preferred esters of the compounds of formula (I) include the compounds in which $R_1$ is replaced by a carboxyl function R-(CO) in which the non-carbonyl moiety R of the ester grouping is selected from hydrogen, straight or branched chain alkyl (e.g., methyl, ethyl, n-propyl, t-butyl, n-butyl), alkoxyalkyl (e.g., methoxymethyl), aralkyl (e.g., benzyl), aryloxyalkyl (e.g., phenoxymethyl), aryl (e.g., phenyl optionally substituted by halogen, $C_{1-4}$ alkyl or $C_{1-4}$ alkoxy); substituted dihydro pyridinyl (e.g., N-methyldihydro pyridinyl); sulphonate esters such as alkyl- or aralkylsulphonyl (e.g., methanesulphonyl); sulfate esters; amino acid esters (e.g., L-valyl or L-isoleucyl) and mono-, di- or triphosphate esters.

Also included within the scope of such esters are esters derived from polyfunctional acids such as carboxylic acids containing more than one carboxyl group, for example, dicarboxylic acids $HO_2C(CH_2)_nCO_2H$ where n is an integer of 1 to 10 (for example, succinic acid) or phosphoric acids. Methods for preparing such esters are well known. See, for example, E. Hahn et al., "Nucleotide dimers as anti-human immunodeficiency virus agents", *Nucleotide Analogues As Antiviral Agents*, J. C. Martin, Ed. Symposium Series #401, American Chemical Society, pp. 156–159 (1989) and M. Busso et al., "Nucleotide dimers suppress HIV expression in vitro", *AIDS Research and Human Retroviruses,* 4(6), pp. 449–455 (1988).

Specific compounds of formula (I) include:

Compound #1

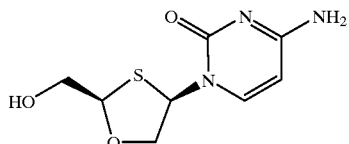

2R-hydroxymethyl-4R-(cytosin-1'-yl)-1,3-oxathiolane;

compound #2:

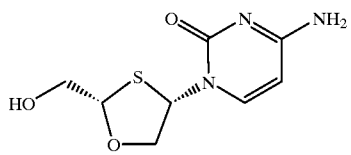

2S-hydroxymethyl-4S-(cytosin-1'-yl)-1,3-oxathiolane;

compound #3:

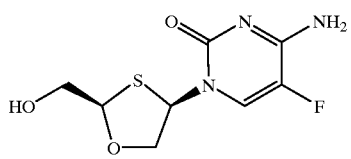

2R-hydroxymethyl-4R-(5'-fluorocytosin-1'-yl)-1,3-oxathiolane; and compound #4

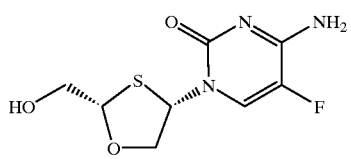

2S-hydroxymethyl-4S-(5'-fluorocytosin-1'-yl)-1,3-oxathiolane; and pharmaceutically acceptable salts and esters thereof.

In the processes for preparing the compounds of this invention, the following definitions are used:

$R_2$ is cytosine or 5-fluorocytosine;

$R_w$ is hydrogen, trisubstituted silyl, $C_{1-6}$ alkyl, aralkyl such as benzyl or trityl, $C_{1-16}$ acyl, preferably a benzoyl or a benzoyl substituted in any position by at least one halogen (bromine, chlorine, fluorine or iodine), $C_{1-6}$ alkyl, $C_{1-6}$ alkoxy, nitro, or trifluoromethyl group;

$R_x$ is $C_{1-6}$ alkyl; and

L is a "leaving group", i.e., an atom or group which is displaceable upon reaction with an appropriate base, with or without a Lewis acid. Suitable leaving groups include acyloxy groups, alkoxy groups, e.g., alkoxy carbonyl groups such as ethoxy carbonyl; halogens such as iodine, bromine, chlorine, or fluorine; amido; azido; isocyanato; substituted or unsubstituted, saturated or unsaturated thiolates, such as thiomethyl or thiophenyl; substituted or unsubstituted, saturated or unsaturated seleno or selenino compounds, such as phenyl selenide or alkyl selenide; and substituted or unsubstituted, saturated or unsaturated aliphatic or aromatic ketones such as methyl ketone.

A suitable leaving group may also be -OR, where R is a substituted or unsubstituted, saturated or unsaturated alkyl group, e.g., $C_{1-6}$ alkyl or alkenyl group; a substituted or unsubstituted aliphatic or aromatic acyl group, e.g., a $C_{1-6}$ aliphatic acyl group such as acetyl and an aromatic acyl group such as benzoyl; a substituted or unsubstituted, saturated or unsaturated alkoxy or aryloxy carbonyl group, such as methyl carbonate and phenyl carbonate; substituted or unsubstituted sulphonyl imidazolide; substituted or unsubstituted aliphatic or aromatic amino carbonyl group, such as phenyl carbamate; substituted or unsubstituted alkyl imidate group such as trichloroacetamidate; substituted or unsubstituted, saturated or unsaturated phosphonates, such as diethylphosphonate; substituted or unsubstituted aliphatic or aromatic sulphonyl group, such as tosylate; or hydrogen.

Oxathiolane compounds of formula (I),

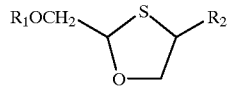
(I)

and pharmaceutically acceptable, salts and esters, may be prepared according to the processes discussed herein or by any method known in the art for the preparation of compounds of analogous structure. The compound of this invention can be produced by the methods described by Mansour et al., "Anti-Human Immunodeficiency Virus and Anti-Hepatitis-B Virus Activities and Toxicities of the Enantiomers of 2'-Deoxy-3'-oxa-4'-thiacytidine and Their 5-Fluoro Analogues in vitro", *J. Med. Chem.*, 1995, Vol. 38, No. 1, pp. 1–4, which is incorporated herein by reference.

In one such process for producing oxathiolanes of this invention, a compound of formula (V),

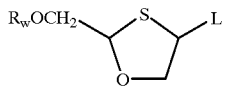
(V)

wherein $R_w$ is hydrogen or a hydroxyl protecting group and L is a displaceable atom or group, i.e., a leaving group, is reacted with an appropriate base.

In a second process for producing oxathiolanes of this invention, a compound of formula (VI)

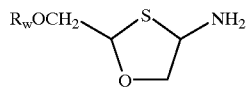
(VI)

may be converted to a compound of formula (I) by conversion of the anomeric $NH_2$ group to the required base by methods well known in the art of nucleoside chemistry.

The 1,3-oxathiolanes of formula (I) may also be prepared, for example, by reaction of an aldehyde of formula (VII)

(VII)

with 2-mercaptoethanol in a compatible organic solvent followed by Pummerer rearrangements as is known in the art (T. Durst, "Dimethylsulfoxide in organic Synthesis", *Adv. Org. Chem.*, E. C. Taylor and B. Wynberg, Eds., 6, pp. 356–365 (1969)) to give 1,3-oxathiolanes of formula (V), which are converted to 1,3-oxathiolanes of formula (I) by methods known in the art of nucleoside chemistry.

Another process for preparing the 1,3-oxathiolanes of formula (I) is illustrated in SCHEME 1.

The various steps involved in the synthesis of 1,3-oxathiolanes of formula (I) as illustrated in SCHEME 1 may be briefly described as follows:

SCHEME 1

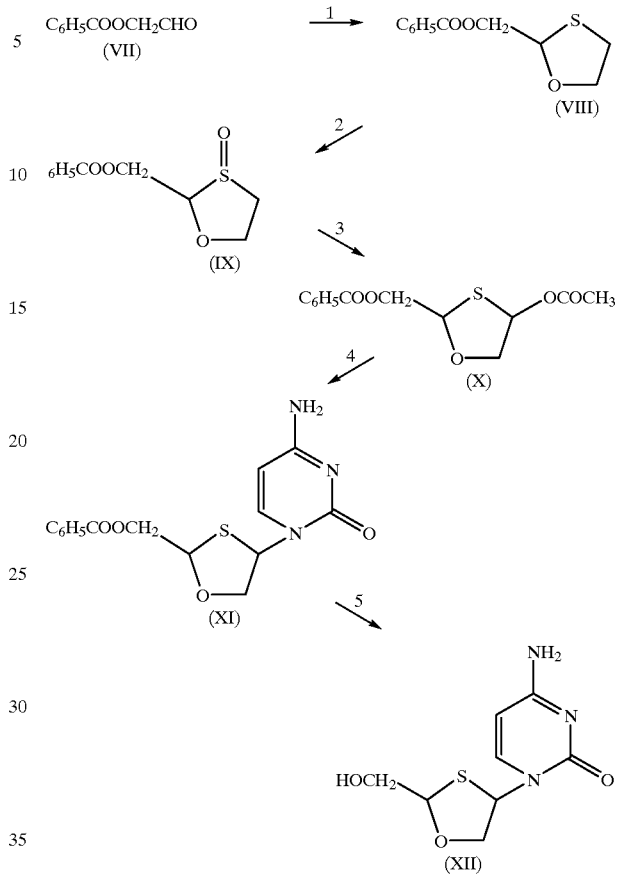

Step 1: Benzoyloxyacetaldehyde of formula (VII) or any aldehyde of the formula $R_wOCH_2CHO$ (C. D. Hurd and E. M. Filiachione, "A new approach to the syntheses of aldehyde sugars", *J. Am. Chem. Soc.*, 61, pp. 1156–1159 (1939)) is condensed with a mercaptoalcohol such as 2-mercaptoethanol in a compatible organic solvent, such as toluene, containing a catalytic amount of a strong acid to give the intermediate shown in formula (VIII).

Step 2: The 1,3-oxathiolane of formula (VIII) is then oxidized with a peracid such as magnesium monoperoxyphthalic acid in a compatible organic solvent such as methylene chloride containing a salt such as tetrabutyl ammonium bromide to give the sulfoxide intermediate shown in formula (IX)

Step 3: The sulfoxide intermediate shown in formula (IX) is treated with an acid anhydride such as acetic anhydride or any other anhydride of the formula $(R_xCO)_2O$ in the presence of a buffer such as tetra-n-butylammonium acetate to give the 2,4-disubstituted-1,3-oxathiolane of formula (X) (T. Durst, *Adv. Org. Chem.*, 6, pp. 356–365 (1969)).

Step 4: The 1,3-oxathiolane of formula (X) is then reacted with a pyrimidine base or analogue thereof, (e.g., cytosine) previously silylated with, for example, hexamethyldisilazane in a compatible solvent using a Lewis acid or trimethylsilyl triflate to give the intermediate of formula (XI) as cis and trans isomers. The isomers may be separated, preferably by chromatography, to give pure cis (XI) and pure trans (XI).

Step 5: The benzoate function of the compound of formula (XI) (cis or trans isomer), is hydrolyzed using a base such as methanolic ammonia to obtain the compound shown in formula (XII) as cis- or trans- isomer. preferably under pressure, to give the product shown in Many of the reactions in the above-described processes have been extensively reported in the context of pyrimidine nucleoside synthesis, for example, in L. B. Townsend, "Synthesis and reaction of pyrimidine nucleoside", *Chemistry of Nucleoside and Nucleotides vol.* 1, Eds., Plenum Press, New York (1989) at pages 1–95, the text of which is incorporated by reference herein.

In the above-described process, the compounds of formula (I) are generally obtained as a mixture of the cis and trans isomers.

The cis and trans isomers may be separated, for example, by acetylation, e.g., with acetic anhydride followed by separation by physical means, e.g., chromatography on silica gel and deacetylation, e.g., with methanolic ammonia or by fractional crystallization.

Resolution of the final product, or an intermediate or starting material therefore may be effected by any suitable method known in the art: see for example, *Stereochemistry of Carbon Compounds*, by E. L. Eliel (McGraw Hill, 1962) and *Tables of Resolving Agents,* by S. H. Wilen.

Where the compound of formula (I) is desired as a single enantiomer it may be obtained either by resolution of the mixture of the two cis enantiomers (by chiral HPLC) or by stereospecific synthesis from isometrically pure starting material or any convenient intermediate. Thus, the compound of formula (I) or any convenient intermediate may be obtained by chiral HPLC using a suitable stationary phase for example acetylated β-cyclodextrin or cellulose triacetate and a suitable solvent for example an alcohol such as ethanol or an aqueous solution such as triethyl ammonioum acetate. Alternatively, the compound of formula (I) or any convenient intermediate may be resolved by enzyme mediated enatioselective catabolism with a suitable enzyme such as cytidine deaminase or selective enzymatic degradation of a suitable derivative using a 5'-nucleotidase for example see Storer et al., "The resolution and Absolute Stereochemistry of the Enantiomers of cis-1[2(Hydroxomethyl)-1,3-Oxathiolan-5-Yl)Cytosine (BCH-189): Equipotent Anti-HIV Agents", *Nucleosides & Nucleotides*, 12(2), 225–236 (1993). When the resolution is effected enzymatically, the enzyme may be employed either in solution or in immobilized form. Enzymes in immobilized form are known in the art for example, by adsorption onto a resin such as Eupergit.

It will be appreciated that the reactions of the above-described processes may require the use of, or conveniently may be applied to, starting materials having protected functional groups, and deprotection might thus be required as an intermediate or final step to yield the desired compound. Protection and deprotection of functional groups may be effected using conventional means. Thus, for example, amino groups may be protected by a group selected from aralkyl (e.g., benzyl), acyl or aryl (e.g., 2,4-dinitrophenyl); subsequent removal of the protecting group being effected when desired by hydrolysis or hydrogenolysis as appropriate using standard conditions. Hydroxyl groups may be protected using any conventional hydroxyl protecting group, for example, as described in "Protective Groups in Organic Chemistry", Ed. J. F. W. McOmie (Plenum Press, 1973) or "Protective Groups in Organic Synthesis" by Theodora W. Greene (John Wiley and Sons, 1981 which is incorporated by reference herein. Examples of suitable hydroxyl protecting groups include groups selected from alkyl (e.g., methyl, t-butyl or methoxymethyl), aralkyl (e.g., benzyl, diphenylmethyl or triphenylmethyl), heterocyclic groups such as tetrahydropyranyl, acyl, (e.g., acetyl or benzoyl) and silyl groups such as trialkylsilyl (e.g., t-butyldimethylsilyl). The hydroxyl protecting groups may be removed by conventional techniques. Thus, for example, alkyl, silyl, acyl and heterocyclic groups may be removed by solvolysis, e.g., by hydrolysis under acidic or basic conditions. Aralkyl groups such as triphenylmethyl may similarly be removed by solvolysis, e.g., by hydrolysis under acidic conditions. Aralkyl groups such as benzyl may be cleaved, for example, by treatment with $BF_3$/etherate and acetic anhydride followed by removal of acetate groups so formed at an appropriate stage in the synthesis. Silyl groups may also conveniently be removed using a source of fluoride ions such as tetra-n-butylammonium fluoride.

Pharmaceutically acceptable salts of the compounds of the invention may be prepared as described in U.S. Pat. No. 4,383,114, the disclosure of which is incorporated by reference herein. Thus, for example, when it is desired to prepare an acid addition salt of a compound of formula (I), the product of any of the above procedures may be converted into a salt by treatment of the resulting free base with a suitable acid using conventional methods. Pharmaceutically acceptable acid addition salts may be prepared by reacting the free base with an appropriate acid optionally in the presence of a suitable solvent such as an ester (e.g., ethyl acetate) or an alcohol (e.g., methanol, ethanol or isopropanol). Inorganic basic salts may be prepared by reacting the free base with a suitable base such as an alkoxide (e.g., sodium methoxide) optionally in the presence of a solvent such as an alcohol (e.g., methanol). Pharmaceutically acceptable salts may also be prepared from other salts, including other pharmaceutically acceptable salts, of the compounds of formula (I) using conventional methods.

A compound of formula (I) may be converted into a pharmaceutically acceptable phosphate or other ester by reaction with a phosphorylating agent, such as $POCl_3$, or a suitable esterifying agent, such as an acid halide or anhydride, as appropriate. An ester or salt of a compound of formula (I) may be converted to the parent compound, for example, by hydrolysis.

The compounds of the invention possess anti-viral activity. In particular these compounds are effective in inhibiting the replication of hepatitis B virus and retroviruses, including human retroviruses such as human immunodeficiency viruses (HIV's), the causative agents of AIDS.

There is thus provided as a further aspect of the invention a compound of formula (I) or a pharmaceutically acceptable derivative thereof for use as an active therapeutic agent in particular as an antiviral agent, for example in the treatment of hepatitis B viral and retroviral infections such as HIV infection.

There is also provided in a further or alternative aspect of this invention, use of a compound of formula (I) or a pharmaceutically acceptable derivative thereof for the manufacture of a medicament for the treatment of a viral infection.

Such viral infections may be, in particular HIV and HBV infections.

In a further or alternative aspect there is provided a method for the treatment of a viral infection, in particular an infection caused by hepatitis B virus or a retrovirus such as HIV, in a mammal, including man, comprising administration of an effective amount of an antiviral compound of formula (I) or a pharmaceutically acceptable derivative thereof.

The compounds of the invention are also useful in the treatment of AIDS-related conditions such as AIDS-related complex (ARC), persistent generalized lymphadenopathy (PGL), AIDS-related neurological conditions (such as dementia), anti-HIV antibody-positive and HIV-positive conditions, Kaposils sarcoma, thrombocytopenia purpura and opportunistic infections.

The compounds of the invention are also useful in the prevention or progression to clinical illness of individuals who are anti-HIV antibody or HIV-antigen positive and in prophylaxis following exposure to HIV.

The compounds of formula (I) or the pharmaceutically acceptable salts and esters thereof, may also be used for the prevention of viral contamination of biological fluids such as blood or semen in vitro.

It will be appreciated by those skilled in the art that references herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general, however, a suitable dose will be in the range from about 1 to about 750 mg/kg of body weight per day, such as 3 to about 120 mg per kilogram body weight of the recipient per day, preferably in the range of 6 to 90 mg/kg/day, most preferably in the range of 15 to 60 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or administered as a bolus containing about 0.1 to about 110 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

The invention thus further provides a pharmaceutical formulation comprising a compound of formula (I) or a pharmaceutically acceptable derivative thereof together with one or more pharmaceutically acceptable carriers thereof and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

The compounds according to the invention may also be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g., sterile, pyrogen-free water, before use.

For topical administration to the epidermis, the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active ingredient in a flavored based, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutically formulations suitable for rectal administration wherein the carrier is a solid, are most preferably represented as unit dose suppositories. Suitable carriers include cocoa butter and other materials commonly used in the art, and the suppositories may be conveniently formed by admixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the compounds of the invention may be used as a liquid spray or dispersible powder or in the form of drops.

Drops may be formulated with an aqueous or non-aqueous base also comprising one or more dispersing agents, solubilizing agents or suspending agents. Liquid sprays are conveniently delivered from pressurized packs.

For administration by inhalation, the compounds according to the invention are conveniently delivered from an insufflator, nebulizer or a pressurized pack or other convenient means of delivering an aerosol spray.

Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions according to the invention may also contain other active ingredients such as antimicrobial agents, or preservatives.

The compounds of the invention may also be used in combination therapy to avoid the production of resistant viral strains.

In particular, the compounds of the invention may also be used in combination with other therapeutic agents, for example, other anti-infective agents. In particular the compounds of the invention may be employed together with known antiviral agents.

The invention thus provides, in a further aspect, a combination comprising a compound of formula (I) or a physiologically acceptable derivative thereof together with another therapeutically active agent, in particular, an antiviral agent.

Suitable therapeutic agents for use in such combinations include nucleoside analogues such as 3TC™, 3'-azido-3'-deoxythymidine (AZT), 2',3'-dideoxycytidine (ddC), 2',3'-dideoxyadenosine, 2',3'-dideoxyinosine (ddI), 3'-deoxythymidine, 2',3'-dideoxy-2',3'-didehydro-thymidine, and 2',3'-dideoxy-2',3'-didehydrocytidine and ribavirin; acyclic nucleosides such as acyclovir, ganciclovir, interferons such as alpha-, beta-and gamma-interferon; glucuronation inhibitors such as probenecid; nucleoside transport inhibitors such as dipyridamole; immunomodulators such as interleukin II (IL2) and granulocyte macrophage colony stimulating factor (GM-CSF), erythropoietin, ampligen, thymomodulin, thymopentin, foscarnet, glycosylation inhibitors such as 2-deoxy-D-glucose, castanospermine, 1-deoxynojirimycin; and inhibitors of HIV binding to CD4 receptors such as soluble CD4, CD4 fragments, CD4-hybrid molecules and inhibitors of the HIV aspartyl protease such as L-735,524.

Suitable further therapeutic agents for use in such combinations also include non nucleoside reverse transcriptase inhibitors such as revirapine, TIBO, HEPT, BHAP, MKC-422, α-APA, TSAO, calanolides, and L-697,661.

Preferably, the further therapeutic agent is selected from: 3TC™, AZT, ddC, and ddI.

The individual components of such combinations may be administered either sequentially or simultaneously in separate or combined pharmaceutical formulations.

The combinations referred to above may conveniently be presented for use in the form of a pharmaceutical formulation and thus pharmaceutical formulations comprising a combination as defined above together with a pharmaceutically acceptable carrier thereof comprise a further aspect of the invention.

When the compound of formula (I) or a pharmaceutically acceptable derivative thereof is used in combination with a second therapeutic agent active against the same virus, the dose of each compound may be either the same or differ from that when the compound is used alone. Appropriate doses will be readily appreciated by those skilled in the art.

It will be further appreciated that the amount of a compound of the invention and the amount of the further therapeutic agent required for use in treatment will vary not only with the particular compound of the invention and the further therapeutic agent selected but also with the route of administration, the nature of the condition being treated and the age and condition of the patient and will be ultimately at the discretion of the attendant physician or veterinarian. In general, however, a suitable dose of the compound of the invention will be in the range from about 1 to about 750 mg/kg of body weight per day, such as 3 to about 120 mg per kilogram body weight of the recipient per day, preferably in the range of 6 to 90 mg/kg/day, most preferably in the range of 15 to 60 mg/kg/day. A suitable dose of the further therapeutic agent will be in the range from about 1 to about 750 mg/kg of body weight per day, such as 3 to about 120 mg per kilogram body weight of the recipient per day, preferably in the range of 6 to 90 mg/kg/day, most preferably in the range of 15 to 60 mg/kg/day.

The desired dose may conveniently be presented in a single dose or as divided doses administered at appropriate intervals, for example as two, three, four or more sub-doses per day.

The invention will be further described by the following examples which are not intended to limit the invention in any way. All temperatures are in degrees Celsius.

EXAMPLES

Example 1

BENZOYLOXYACETALDEHYDE

$C_6H_5COOCH_2CHO$ (VII)

This known intermediate was prepared by portionwise addition of $NaIO_4$ (80 g) to a mixture of 1-benzoyl glycerol (50 g), $CH_2Cl_2$ (500 ml), and $H_2O$ (25 ml) under vigorous stirring at room temperature. The resulting solution was stirred for 2 hours, $MgSO_4$ (100 g) was added and the solution stirred for an additional 30 minutes. The mixture was filtered, the filtrate evaporated in vacuo and the residue distilled in vacuo to yield 26 g of pure product.

b.p. 92–94°/0.25 mm $^1$H NMR (200 MHz; TMS as internal reference):

δ(ppm in $CDCl_3$)

9.71 (s, 1 H; —CHO)

8.11 (d, 2 H; aromatic)

7.60 (m, 1 H; aromatic)

7.46 (m, 2 H; aromatic)

4.88 (s, 2 H; —CH$_2$CHO)

Example 2

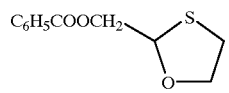

2-BENZOYLOXYMETHYL-1,3-OXATHIOLANE (VIII)

A mixture of benzoyloxyacetaldehyde (example 1) (6.21 g), 2-mercaptoethanol (3 ml) and para-toluene sulfonic acid (0.2 g) in toluene (150 ml) was heated for 3 hours at refluxing under water removal conditions using a Dean Stark apparatus. The mixture was cooled to room temperature, washed first with aqueous $NaHCO_3$-solution (1 ×50 ml), and then with water (2.5 ml) and dried over $MgSO_4$. The solution was filtered and the filtrate evaporated under reduced pressure. The residue was purified on silica gel using hexane:ethyl acetate (9:1) as eluant. It yielded 7.63 g (90%) of pure product, which was identified by $^1H$- and $^{13}C$—NMR.

$R_f$: 0.39 (hexane:ethyl acetate)
$^1H$—NMR: δ (ppm in $CDCl_3$)
 8.03 (m, 2 H, aromatic)
 7.53 (m, 1 H, aromatic)
 7.39 (m, 2 H, aromatic)
 5.41 (dd, 1 H, $C_2$-H)
 4.43 (m, 2 H, $C_2$-$CH_2OCC_6H_5$)
 4.21 (m, 1 H, $C_5$-H)
 3.96 (m, 1 H, $C_5$-H)
 2.98 (m, 2 H, $C_4$-H)
$^{13}C$—NMR: δ (ppm in $CDCl_3$)
 166.82, 133.74, 130.35, 128.97, 83.58, 71.87, 66.62 and 32.74

Example 3

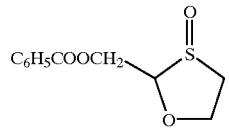

2-BENZOYLOXYMETHYL-3-OXO-1,3-OXATHIOLANE (IX)

Monoperoxyphthalic acid, magnesium salt (MMPP, 28 g) was added portionwise under vigorous stirring to a mixture of 2-benzoyloxymethyl-1,3-oxathiolane (example 2) (20 g), tetrabutyl ammonium bromide (0.4 g) in methylene chloride (200 ml), and water (200 ml). The mixture was stirred at room temperature for 30 minutes and the organic layer was collected. The aqueous phase was extracted with methylene chloride (3 x 75 ml) and the combined organic layer was washed first with water (2 x 100 ml), then with brine solution (100 ml), dried over MgSO4, and filtered. The filtrate was evaporated in vacuo and the residue was purified by chromatography on silica gel using ethyl acetate as eluant to give 18.5 g (86%) of pure product as a mixture of cis- and trans-isomers in a ratio of 1:2 respectively.
m.p.: 70–72°
$^1H$-NMR: δ (ppm in $CDCl_3$)
 8.05 (m, 2 H, aromatic, cis-isomer)
 7.95 (m, 2 H, aromatic, trans-isomer)
 7.56 (m, aromatic)
 7.23 (m, aromatic)
 4.77 (m, 4 H, $C_2$-H, $C_5$-H, and $C_2$-$CH_2OOCC_6H_5$)
 4.43 (m, 1 H, $C_5$-H, trans-isomer)
 4.09 (m, 1 H, $C_5$-H, cis-isomer)
 3.11 (m, 2 H, $C_4$-H, trans-isomer)
 2.75 (m, 2 H, $C_4$-H, cis-isomer)
$^{13}C$—NMR: δ (ppm in $CDCl_3$)
cis-isomer:
 166.64, 134.02, 130.42, 129.88, 129.06, 96.16, 68.83, 59.47 and 54.30
trans-isomer:
 166.36, 134.12, 130.29, 129.68, 129.15, 108.07, 70.09, 61.83 and 53.47

Example 4

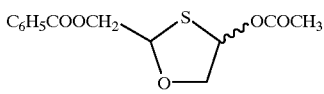

2-BENZOYLOXYMETHYL-4-ACETOXY-1,3-OXATHIOLANE (X)

A mixture of 2-benzoyloxymethyl-3-oxo-1,3-oxathiolane (example 3) (10.5 g), tetra-n-butylammonium acetate (17 g) in acetic anhydride (250 ml) was heated at 110 to 120° C. under argon for 14 hours and cooled to room temperature. Excess acetic anhydride was removed under reduced pressure. The residue was dissolved in methylene chloride (500 ml), washed first with saturated aqueous $NaHCO_3$ (2×200 ml), then with brine solution (200 ml), dried over $MgSO_4$, filtered and evaporated in vacuo. The residue was purified by chromatography on silica gel using hexane:ethyl acetate (8:1) as eluant to give 7.4 g (60% yield) of the desired product as a mixture of cis-and trans- isomers. A small quantity of each isomer was also isolated and characterized by $^1H$- and $^{13}C$—NMR.

cis-isomer:
$R_f$: 0.43 (hexane:EtOAc)
$^1H$—NMR: δ (ppm in $CDCl_3$)
 8.05 (m, 2 H, aromatic)
 7.58 (m, 1 H, aromatic)
 7.45 (m, 2 H, aromatic)
 6.24 (d, 1 H, $C_4$-H)
 5.50 (t, 1 H, $C_2$-H)
 4.61 (d, 1 H, $C_2$-$CH_2OOCC_6H_5$)
 4.53 (d, 2 H, $C_5$-H)
 3.94 (dd, 1 H, $C_5$-H)
 2.05 (s, 3 H, $CH_3$)
trans-isomer:
$R_f$: 0.43 (hexane:EtOAc 7:3)
$^1H$—NMR: δ (ppm in $CDCl_3$)
 8.04 (m, 2 H, aromatic)
 7.58 (m, 1 H, aromatic)
 7.45 (m, 2 H, aromatic)
 6.27 (dd, 1 H, $C_4$-H)
 5.73 (dd, 1 H, $C_2$-H)
 4.53 (dd, 1 H, $C_2$-$CH_2OOCC_6H_5$)
 4.34 (dd, 1 H, $C_5$-H)
 4.26 (dd, 1 H, $C_2$-$CH_2OCC_6H_5$)
 4.20 (dd, 1 H, $C_5$-H)
 2.09 (s, 3 H, $CH_3$)

$^{13}$C—NMR: δ (ppm in CDCl$_3$)
  177.66, 166.37, 133.46, 129.93, 128.60, 83.76, 81.22, 74.33, 64.65 and 20.79

Example 5

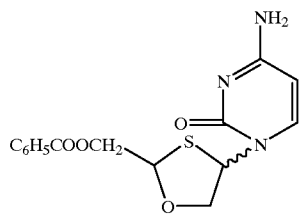

(XXXI)

CIS- AND TRANS-2-BENZOYLOXYMETHYL-4-(CYTOSIN-1'-YL)-1,3-OXATHIOLANE

A mixture of cytosine (206 mg), ammonium sulfate (10 mg) and hexamethyldisilazane (HMDS, 10 ml) was heated at refluxing under argon until a clear solution resulted. Excess reagents were evaporated in vacuo and the remaining volatile removed under high vacuum (15 minutes). The solid residue was dissolved in dry methylene chloride (20 ml) and a solution of 2-benzoyloxymethyl-4-acetoxy-1,3-oxathiolane (example 4) (350 mg) in dry methylene chloride (20 ml) was added under argon, followed by a solution of tin IV chloride (SnCl$_4$, 124 ml) in methylene chloride (20 ml) at 0° C. The reaction mixture was stirred under argon overnight at room temperature, then heated at refluxing for 3 hours and cooled to room temperature. The mixture was diluted with methylene chloride (100 ml) and poured while stirring into saturated aqueous NaHCO$_3$. The organic layer was separated by filtration over celite, washed first with water (2×75 ml), then with brine solution (100 ml), dried over MgSO$_4$ and filtered. The residue was purified by chromatography on silica gel using ethyl acetate:CH$_3$OH as the eluant to give 140 mg (35%) of the desired product as a mixture of cis- and trans- isomers in a 1:1 ratio as determined by $^1$H—NMR. These isomers were separated as the N-acetyl derivatives in the next example.

Example 6

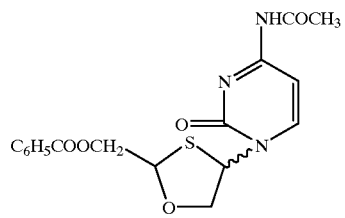

(XXXII)

CIS- AND TRANS-2-BENZOYLOXYMETHYL-4-(N4'-ACETYL-CYTOSIN-1'-YL)-1,3-OXATHIOLANE

A solution of the cis- and trans- mixture of 2-benzoyloxymethyl-4-(cytosin-1'-yl)-1,3-oxathiolane (example 5) (135 mg), 4-dimethylaminopyridine (DMAP, 15 mg) and acetic anhydride (44 ml) in dry pyridine (10 ml) was stirred overnight at room temperature (16 hours) and poured into cold water (100 ml) followed, by extraction with methylene chloride (3×50 ml). The extract was washed with water, dried over MgSO$_4$, filtered and evaporated in vacuo. Toluene was added to the residue, then evaporated in vacuo. Toluene was added to the residue, then evaporated in vacuo and the residual oil was purified by chromatography on silica gel using ethyl acetate as eluant to yield 65 mg of pure trans-isomer as the fast moving product and 60 mg of pure cis-isomer as the low moving product. These were characterized by $^1$H and $^{13}$C—NMR.

cis-isomer:
$^1$H-NMR: δ (ppm in CDCl$_3$)
  9.61 (b, 1 H, C$_4$'-NHCOCH$_3$)
  8.29 (d, 1 H, C$_6$'-H)
  8.06 (m, 2 H, aromatic)
  7.65 (m, 1 H, aromatic)
  7.51 (m, 2 H, aromatic)
  7.25 (d, 1 H, C$_5$'-H)
  6.61 (d, 1 H, C$_4$-H)
  5.50 (t, 1 H, C$_2$-H)
  4.80 (m, 2 H, C$_2$-CH$_2$OOCC$_6$H$_5$)
  4.48 (d, 1 H, C$_5$-H)
  4.05 (dd, 1 H, C$_5$-H)
  2.25 (s, 3 H, CH$_3$)
$^{13}$C—NMR: δ (ppm in CDCl$_3$)
  170.93, 166.28, 162.80, 155.76, 146.06, 133.91, 129.90, 128.84, 97.45, 85.88, 78.25, 64.60, 63.53 and 24.71.

trans-isomer:
$^1$H—NMR: δ (ppm in DMSO d$_6$)
  10.88 (s, 1 H, C$_4$'-NHCOCH$_3$)
  8.13 (d, 1 H, C$_6$'-H)
  7.96 (m, 2 H, aromatic)
  7.68 (m, 1 H, aromatic)
  7.52 (m, 2 H, aromatic)
  7.20 (d, 1 H, C$_5$'-H)
  6.35 (d, 1 H, C$_4$-H)
  5.96 (dd, 1 H, C$_2$-H)
  4.58 (dd, 1 H, C$_2$-CH$_2$OOCC$_6$H$_5$)
  4.44 (d, 1 H, C$_5$-H)
  4.29 (m, 2 H, C$_5$-H and CH$_2$OOCC$_6$H$_5$)
  2.07 (s, 3 H, CH$_3$)
$^{13}$C—NMR: δ (ppm in DMSO d$_6$)
  171.53, 165.84, 162.76, 155.21, 146.59, 134.00, 129.64, 129.23, 96.54, 83.78, 74.24, 64.58, 64.01 and 24.35

Example 7

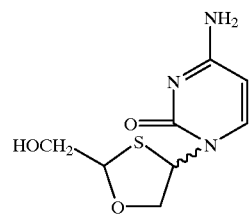

(XXXIII)

CIS- AND TRANS-2-HYDROXYMETHYL-4-(CYTOSIN-1'-YL)-1,3-OXATHIOLANE cis-isomer (BCH-270):
A solution of cis-2-benzoyloxymethyl-4(N4'-acetyl-cytosin-1'-yl)-1,3-oxathiolane (example 6) (54 mg) in methanolic ammonia (50 ml) was stirred overnight at room temperature (16 hours). The solvent was evaporated in vacuo and the residue treated with ether yielding 37 mg (90%) of desired product. The product was then characterized by $^1$H- and $^{13}$C—NMR.

m.p.: 213–215° C.
UV:(CH$_3$OH) Lamda max: 270 nm
$^1$H—NMR: δ (ppm in, DMSO d$_6$)
  7.85 (d, 1 H, C$_6$-H)
  7.16 (d, 2 H, C$_4$-NH$_2$)
  6.34 (d, 1 H, C$_4$-H)
  5.76 (d, 1 H, C$_5$-H)
  5.31 (t, 1 H, C$_2$-CH$_2$OH)
  5.18 (t, 1 H, C$_2$-H)
  4.40 (d, 1 H, C$_5$-H)
  3.92 (dd, 1 H, C$_5$-H)
  3.78 (m, 2 H, C$_2$-CH$_2$OH)
$^{13}$C—NMR: δ (ppm in DMSO d$_6$)
  165.95, 155.74, 142.39, 94.98, 88.85, 77.29, 62.91 and 62.48
trans-isomer:

A solution of trans-2-benzoyloxymethyl-4-(N$_4$-acetyl-cytosin-1'-yl)-1,3-oxathiolane (example 6) (63 mg) in methanolic ammonia (50 ml) was stirred overnight at vacuo and the residue was solidified with ether to give 36 mg (93%) of the desired product which was characterized by $^1$H- and $^{13}$C—NMR.
m.p.: 175–177° C.
UV:(CH$_3$OH) Lamda max: 270 nm
$^1$H—NMR: δ (ppm in DMSO d$_6$)
  7.67 (d, 1 H, C$_6$-H)
  7.19 (d, 2 H, C$_4$-NH$_2$)
  6.30 (d, 1 H, C$_4$-H)
  5.77 (d, 1 H, C$_5$-H)
  5.56 (t, 1 H, C$_2$-CH$_2$OH)
  5.23 (t, 1 H, C$_2$-H)
  4.18 (m, 2 H, C$_5$-H)
  3.61 (m, 1 H, C$_2$-CH$_2$OH)
  3.36 (m, 1 H, C$_2$-CH$_2$OH)
$^{13}$C—NMR: δ (ppm in DMSO d$_6$)
  166.00, 155.65, 142.30, 95.11, 87.52, 74.52, 63.42 and 62.86

Example 8

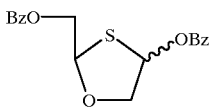

CIS AND TRANS-2-BENZOYLOXYMETHYL-4-BENZOYLOXY-1,3-OXATHIOLANE

2-Benzoyloxymethyl-1,3-oxathiolane example 2) (0.4 g, 1.78 mmol) was dissolved in 200 mL of degased dry benzene under a stream of argon. To this solution was added benzoyl peroxide (0.863 g, 3.56 mmol) and AIBN catalyst (15 mg, 0.09 mmol, 5%) in one portion. The resulting mixture was refluxed for 4 hours under argon. The solvent was then removed under high vacuum, and the residue was dissolved in dichloromethane (40 ml), extracted 2× with a solution of 10% sodium bicarbonate (15 mL) and dried over MgSO$_4$. Evaporation of dichloromethane under reduced pressure and purification of the residue on silica gel column using ethyl acetate; hexane (30%) as eluant afforded the pure mixture of cis- and trans-1,3-oxathiolane derivative as a colorless oil (264 mg, 0.76 mmol, 43% yield). The trans isomer was separated as a white solid m.p. 60–62° C. This mixture was fully characterized by $^1$H, and $^{13}$C NMR spectrum. R$_f$=0.43 (ethyl acetate:hexanes 1:4).

1 H NMR δ (ppm in CDCl$_3$): 8.07 (m, 2 H, aromatic), 7.59 (m, 1 H, aromatic), 7.56 (m, 2 H, aromatic), 6.51 (t, 1 H, C$_4$-H), 5.79 (m, 1 H, C$_2$-H), 4.63 (m, 2 H, CH$_2$-OCOPh), 4.32 (m, 2 H, C$_5$-H) . 13 C NMR δ(ppm in CDCl$_3$) : 166.56, 166.36, 134.12, 133.78, 130.35, 129.04, 84.40, 82.53, 75.04, 65.33, 39.89, 25.43, 23.93.

Example 9

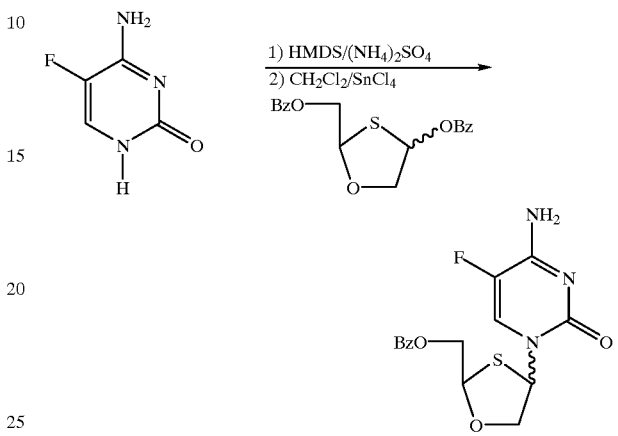

CIS AND TRANS-2-BENZOYLOXYMETHYL-4-(5'-FLUOROCYTOSIN-1'-YL)-1,3-OXATHIOLANE 5-fluorocytosine (700 mg, 5.4 mmol) was heated at reflux HMDS(1,1,1,3,3,3-hexamethyldisilazane, 30 ml) containing catalytic amount of ammonium sulfate (20 mg) for overnight (16 h). The clear solution was evaporated to dryness under reduced pressure and the residue was dissolved in dry methylene chloride (50 ml). To this solution was added through a cannula a mixture of 2-benzoyloxymethyl-4-benzoyloxy-1,3-oxathiolane (example 8) (1.25 g, 3.63 mmol) in dry methylene chloride (50 ml), followed by adding tin tetrachloride (4 ml of 1 M solution in methylene chloride). The reaction mixture was stirred under argon atmosphere at room temperature for 16 h and heated at reflux for 1 h. After cooling to room temperature the mixture was poured into saturated aqueous NaHCO$_3$ solution (150 ml), stirred for 15 min. and filtered over celite. The organic layer was collected. The aqueous solution was further extracted with methylene chloride (2×100 ml). The combined organic phase was washed twice with water (2×150 ml), once with brine solution, dried over Na$_2$SO$_4$, and filtered. Solvent was removed under reduced pressure. The residue contained two compounds in a ratio of 2:3 for cis and trans isomers and was purified on silica gel using ethyl acetate-methanol 95:5 as eluant to give 280 mg of cis isomer and 420 mg of trans isomer for a total yield of 53%.

Cis isomer:
Mp.: 235–236° C. (dec.).
R$_f$ : 0.36 (EtOAc:MeOH 9:1)
$^1$H—NMR (300 MHz, DMSO-d$_6$): δ in ppm: 7.94 (m, 2 H, aromatic), 7.80 (d, 2 H, H-6' and 1 H of NH$_2$ underneath, J$_{H-F}$=6.8 Hz), 7.68 (m, 1 H, aromatic), 7.58 (b, 1 H of NH$_2$), 7.47 (m, 2 H, aromatic), 6.28 (d, 1 H, H-4, J=3.0 Hz), 5.51 (t, 1 H, H-2, J=3.8 Hz), 4.73 (m, 2 H, -CH$_2$OBz), 4.61 (d, 1 H, H-5, J=11 Hz) and 3.98 (dd, 1 H, H-5, J=4.7 and 11 Hz).

Trans-isomer:
Mp.: 235–236° C. (dec.).
$^1$H—NMR (300 MHz, DMSO-d$_6$): δ in ppm: 7.97 (m, 2 H, aromatic), 7.81 (d, 2 H, H-6' and 1 H of NH$_2$ underneath, $J_{H-F}$=7.1 Hz), 7.66 (m, 1H, aromatic), 7.55 (m, 3 H, 2 H of aromatic and 1 H of NH$_2$), 6.32 (d, 1 H, H-4, J=4.8 Hz), 6.02 (dd, 1 H, H-2, J=3.2 and 8.5 Hz), 4.55 (dd, 1 H, -CH$_2$OBz, J=8.4 and 11.9 Hz), 4.38 (d, 1 H, H-5, J=10.2 Hz) and 4.26 (dd, 2 H, 1 H of H-5 and 1 H of -CH$_2$OBz, J=3.6 and 10.5 Hz).

Example 10

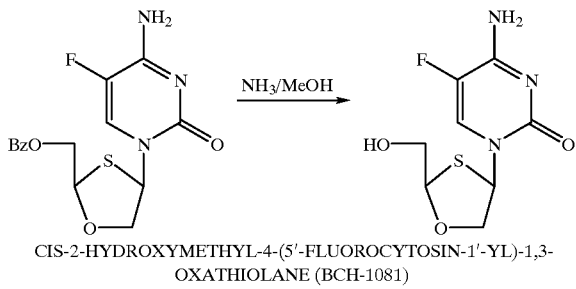

CIS-2-HYDROXYMETHYL-4-(5'-FLUOROCYTOSIN-1'-YL)-1,3-OXATHIOLANE (BCH-1081)

Cis-2-benzoyloxymethyl-4-(5'-fluorocytosin-1'-yl)-1,3-oxathiolane (example 9) (75 mg , 0.21 mmol) was dissolved in methanolic ammonia (25 ml). The mixture was stirred at room temperature for 16 h and solvents were removed under reduced pressure. The residue was triturated with ether (2×20 ml). The remaining solid was recrystallized in ethanol-ether to give the desired compound (43 mg) in 80% yield.

M.p.: >210° C. (dec.)

$R_f$: 0.41 (EtOAc:MeOH 4:1)

UV: λmax (H$_2$O): 284 nm $^1$H—NMR (300 MHz, DMSO-d$_6$): δ in ppm: 8.14 (d, 1 H, H-6', $J_{H-F}$=7.1 Hz), 7.79 (bs, 1 H, NH$_2$, D$_2$O exchangeable), 7.56 (bs, 1 H, NH$_2$, D$_2$O exchangeable), 6.28 (d, 1 H, H-4, J=2.6 Hz), 5.44 (t, 1 H, OH, D$_2$O exchangeable), 5.18 (t, 1 H, H-2, J=5.5 Hz), 4.44 (d, 1 H, H-5, J=10.5 Hz), 3.91 (dd, 1 H, H-5, J=4.6 and 10.6 Hz), and 3.78 (m, 2 H, CH$_2$OH)

Example 11

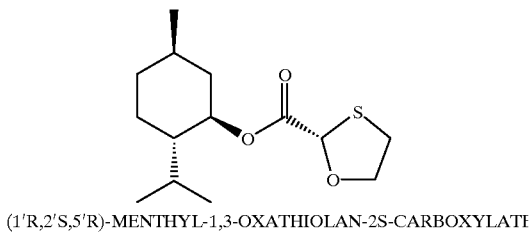

(1'R,2'S,5'R)-MENTHYL-1,3-OXATHIOLAN-2S-CARBOXYLATE

To a mixture of (1'R,2'S, 5'R)-menthyl-5S-acetoxy-1,3-oxathiolan-2S-carboxylate (WO 92/20669, enclosed herewith by reference) (1.0 g, 3.03 mmol) and triethylsilane (4.84 ml, 30.3 mmol) at room temperature under an argon atmosphere was added trimethylsilyl trifluoromethanesulfonate (0.584 ml, 3.03 mmol). The reaction mixture was stirred at room temperature for 12 h and then diluted with dichloromethane (150 ml), washed with saturated aqueous solution of NaHCO$_3$, water, brine, dried over sodium sulfate and concentrated. Chromatography (Hexane-EtOAc, 6:1) of the crude product gave the product (0.71 g, 87%) as colorless oil: $^1$H NMR in CDCl$_3$: δ0.45–2.10 (m, 17 H), 2.96–3.20 (m, 2 H), 4.20–4.40 (m, 1 H), 4.72 (dt, 1 H), 5.45 (s, 1 H); [α]$_D^{25}$ -102.9° (c, 1.02, CHCl$_3$).

Example 12

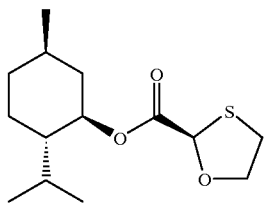

(1'R,2'S,5'R)-MENTHYL-1,3-OXATHIOLAN-2R-CARBOXYLATE

To a mixture of (1'R,2'S, 5'R)-menthyl-5 S-acetoxy-1,3-oxathiolan-2R-carboxylate (WO 92/20669) (0.50 g, 1.51 mmol) and triethylsilane (2.42 ml, 15.1 mmol) at room temperature under an argon atmosphere was added trimethylsilyl trifluoromethanesulfonate (0.29 ml, 1.51 mmol). The reaction mixture was stirred at room temperature for 12 h and then diluted with dichloromethane (125 ml), washed with saturated aqueous solution of NaHCO$_3$, water, brine, dried over sodium sulfate and concentrated. Chromatography (Hexane-EtOAc, 6:1) of the crude product gave the product (0.369 g, 86%) as colorless oil: $^1$H NMR in CDCl$_3$: δ0.40–2.10 (m, 17 H), 2.98–3.19 (m, 2 H), 4.20–4.40 (m, 2 H), 4.72 (dt, 1 H), 5.46 (s, 1 H).

Example 13

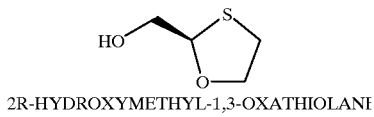

2R-HYDROXYMETHYL-1,3-OXATHIOLANE

To a solution of (1'R,2'S, 5'R)-menthyl-1,3-oxathiolan-2R-carboxylate (example 12) (3.23 g, 11.9 mmol)in anhydrous ethanol (20 ml) at 0° C. under an argon atmosphere were added sodium borohydride (1.12 g, 29.7 mmol) and anhydrous methanol (0.916 ml, 47.6 mmol). The reaction mixture was stirred at 0° C. for 1 h and allowed to warm to room temperature and stirred for 12 h. The reaction was then quenched with acetic acid and the solvent was removed in vacuo. The obtained residue was diluted with dichloromethane (225 ml), washed with water, brine, dried over sodium sulfate and concentrated. Chromatography (Hexane-Et$_2$O, 1:1) of the crude product gave the product (1.30 g, 91%) as colorless oil: $^1$H NMR in CDCl$_3$ δ2.85–2.97 (m, 2 H), 3.58 (dd, 1 H, J=12.2, 5.4 Hz), 3.66 (dd, 1 H, J=12.2, 3.3 Hz), 3.75–3.85 (m, 1 H), 4.14–4.25 (m, 1 H), 5.16 (dd, 1 H, J=5.4, 3.3 Hz)

Example 14

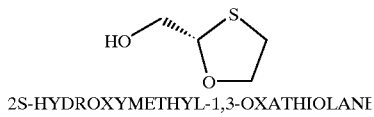

2S-HYDROXYMETHYL-1,3-OXATHIOLANE

To a solution of (1'R,2'S, 5'R)-menthyl-1 -oxathiolan-2 S-carboxylate (example 11) (1.16 g, 4.26 mmol) in anhydrous ethanol (10 ml) at 0° C. under an argon atmosphere were added sodium borohydride (0.403 g, 10.7 mmol) and anhydrous methanol (0.690 ml, 17.03 mmol). The reaction mixture was stirred at 0° C. for 1 h and allowed to warm to room temperature and stirred for 12 h. The reaction was then quenched with acetic acid and the solvent was removed in vacuo. The obtained residue was diluted with dichloromethane (150 ml), washed with water, brine, dried over sodium sulfate and concentrated. Chromatography (Hexane-Et$_2$O, 1:1) of the crude product gave the product (0.47 g, 92%) as colorless oil: $^1$H NMR in CDCl$_3$ : δ2.85–2.99 (m, 2 H), 3.60 (dd, 1 H, J=12.2, 5.5 Hz), 3.65 (dd, 1 H, J=12.2, 3.3 Hz), 3.80–3.90 (m, 1 H), 4.20–4.30 (m, 1 H), 5.15 (dd, 1 H, J=5.5, 3.3 Hz); [α]D$^{25}$ –35.6° (c, 1.25, CHCl$_3$).

Example 15

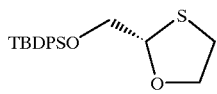

2S-t-BUTYLDIPHENYLSILYLOXYMETHYL-1,3-OXATHIOLAN

To a solution of 2S-hydroxymethyl-1,3-oxathiolane (example 14) (0.63 g, 5.3 mmol), imidazole (0.71 g, 10.4 mmol) in tetrahydrofuran (15 ml) at 0° C. under an argon atmosphere was added a solution of t-butyldiphenylsilyl chloride (2.16 g, 7.9 mmol) in tetrahydrofuran (8 ml). The reaction mixture was allowed to warm to room temperature and stirred for 12 h then diluted with dichloromethane (125 ml). The organic layer was washed with water, brine, dried over sodium sulfate and concentrated. Chromatography (Hexane-EtOAc, 6:1) of the crude product gave the product ( 1.87 g, 99%) as colorless oil: $^1$H NMR in CDCl$_3$ : δ1.08 (s, 9 H), 2.93–2.99 (m, 2 H), 3.70 (dd, 1 H, J=10.9, 4.6 Hz), 3.86 (dd, 1 H, J=10.9, 6.4 Hz), 3.94–4.15 (m, 2 H), 5.29 (dd, 1 H, J=6.4, 4.6 Hz), 7.35–7.50 (m, 6 H), 7.68–7.75 (m, 4 H), [α]D$^{25}$ –23.3° (c, 1.0, CHCl$_3$).

Example 16

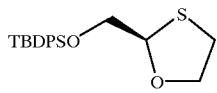

2R-t-BUTYLDIPHENYLSILYLOXYMETHYL-1,3-OXATHIOLAN

To a solution of 2R-hydroxymethyl-1,3-oxathiolane (example 1 ) (1.30 g, 10.8 mmol), imidazole (1.47 g, 21.6 mmol) in tetrahydrofuran (30 ml) at 0° C. under an argon atmosphere was added a solution of t-butyldiphenylsilyl chloride (4.46 g, 16.2 mmol) in tetrahydrofuran (15 ml). The reaction mixture was allowed to warm to room temperature and stirred for 12 h, then diluted with dichloromethane (150 ml). The organic layer was washed with water, brine, dried over sodium sulfate and concentrated. Chromatography (Hexane-EtOAc, 6:1) of the crude product gave the product ( 3.64 g, 94%) as colorless oil: $^1$H NMR in CDCl$_3$ : δ1.04 (s, 9 H), 2.89–2.99 (m, 2 H), 3.65 (dd, 1 H, J=10.9, 4.6 Hz), 3.88 (dd, 1 H, J=10.9, 6.4 Hz), 3.90–4.14 (m, 2 H), 5.27 (dd, 1 H, J=6.4, 4.6 Hz), 7.34–7.46 (m, 6 H), 7.64–7.74 (m, 4 H).

Example 17

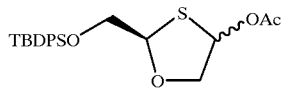

TRANS AND CIS-2R-t-BUTYLDIPHENYLSILYLOXYMETHYL 4-ACETOXY-1,3-OXATHIOLANE

Solid meta-chloroperbenzoic acid (MCPBA) (0.23 g, 80%, 1.06 mmol) was added to a stirred solution of 2R-t-butyldiphenylsiloxymethyl-1 ,3-oxathiolane (example 16) (0.32 g, 0.89 mmol) in dichloromethane (20 ml) at 0° C. The reaction mixture was stirred at 0° C. for 2 h and then diluted with dichloromethane (150 ml), washed with saturated aqueous Na$_2$CO$_3$ solution, water, brine, dried over sodium sulfate and concentrated. Chromatography of the crude product gave a mixture of sulfoxides. The mixture of the obtained sulfoxide, acetic anhydride (10 ml), tetrabutyl ammonium acetate ( 0.32 g , 1.06 mmol) was then heated at 120° C. for 6 h and the excess acetic anhydride was removed in vacuo. The residue was diluted in dichloromethane (150 ml), washed with water, brine, dried over sodium sulfate and concentrated. Chromatography of the crude product gave a mixture of acetate (0.164 g, 45%) as colorless oil: $^1$H NMR in CDCl$_3$: δ1.05 (s, 9 H), 2.03 (s, 1.35 H), 2.08 (s, 1.65 H), 3.60–4.50 (m, 4 H), 5.28 (t, 0.45 H, J=5.4 Hz), 5.55 (dd, 0.55 H, J=6.5, 4.7 Hz), 6.14–6.20 (m, 1 H), 7.30–7.50 (m, 6 H), 7.60–7.78 (m, 4 H).

Example 18

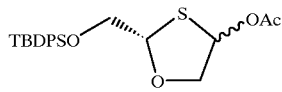

TRANS AND CIS-2S-t-BUTYLDIPHENYLSILYLOXYMETHYL 4-ACETOXY-1,3-OXATHIOLANE

Solid MCPBA (0.85 g, 80%, 3.9 mmol) was added to a stirred solution of 2S-t-butyldiphenylsiloxymethyl-1,3-oxathiolane (example 15) (1.35 g, 3.9 mmol) in dichloromethane (30 ml) at 0° C. The reaction mixture was stirred at 0° C. for 2 h and then diluted with dichloromethane (225 ml), washed with saturated aqueous Na$_2$CO$_3$ solution, water, brine, dried over sodium sulfate and concentrated. Chromatography of the crude product gave a mixture of sulfoxides. The mixture of the obtained sulfoxide, acetic anhydride (15 ml), tetrabutyl ammonium acetate (1.19 g , 3.9 mmol) was then heated at 120° C. for 6 h and the excess acetic anhydride was removed in vacuo. The residue was diluted with dichloromethane (200 ml), washed with water, brine, dried over sodium sulfate and concentrated. Chromatography of the crude product gave a mixture of acetate (0.601 g, 40%) as colorless oil: $^1$H NMR in CDCl$_3$: δ1.10 (s, 9 H), 2.05 (s, 1.2 H), 2.10 (s, 1.8 H), 3.60–4.50 (m, 4 H), 5.30 (t, 0.4 H, J=5.5 Hz), 5.58 (dd, 0.6 H, J=6.5, 4.8 Hz), 6.14–6.23 (m, 1 H), 7.33–7.50 (m, 6 H), 7.65–7.78 (m, 4 H).

Example 19

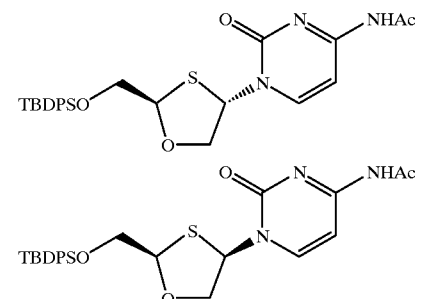

2R-t-BUTYLDIPHENYLSILYLOXYMETHYL-4S-(N-4'-ACETYLCYTOSIN-1'-YL)-1,3-OXATHIOLANE AND
2R-t-BUTYLDIPHENYLSILYLOXYMETHYL-4R-(N-4'-ACETYLCYTOSIN-1'-YL)-1,3-OXATHIOLANE 2,6-lutidine (0.054 ml, 0.49 mmol) and trimethylsilyl trifluoromethanesulfonate (0.095 ml, 0.49 mmol) were added to a suspension of N-4'-acetylcytosine (0.045 g, 0.29 mmol) in dichloroethane (2 ml) at room temperature under argon atmosphere. The mixture was stirred for 15 min and mixture of cis and trans 2R-t-butyldiphenylsiloxymethyl-4-acetoxy-1, 3-oxathiolane (example 17) (0.100 g, 0.25 mmol) in dichloroethane (2 ml) and trimethylsilyl trifluoromethanesulfonate (0.048 ml, 0.25 mmol) were introduced successively. The reaction mixture was heated to reflux for half hour and diluted with dichloromethane, washed with saturated aqueous NaHCO$_3$ solution, water, brine, dried over sodium sulfate and concentrated. Chromatography of the crude product gave a mixture of trans and cis isomer which was subjected to preparative TLC separation to give cis isomer (33 mg, 26%) [$^1$H NMR in CDCl$_3$: δ1.08 (s, 9 H), 2.22 (s, 3 H), 3.85–4.45 (m, 4 H), 5.26 (t, 1 H, J=4.3 Hz), 6.54 (d, 1 H, J=4.2 Hz), 7.21 (d,1 H, J=7.4 Hz), 7.35–7.50 (m, 6 H), 7.60–7.75 (m, 4 H), 8.23 (d, 1 H, J=7.4 Hz), 9.02 (bs, 1 H)] and trans isomer (49 mg, 39%) [$^1$H NMR in CDCl$_3$: δ1.04 (s, 9 H), 2.21 (s, 3 H), 3.56–4.26 (m, 4 H), 5.64 (dd, 1 H, J=6.8, 4.4 Hz), 6.39 (d, 1 H, J=3.6 Hz), 7.31–7.48 (m, 7 H), 7.58–7.71 (m, 4 H), 8.01 (d, 1 H, J=7.4 Hz), 8.86 (bs, 1 H)].

Example 20

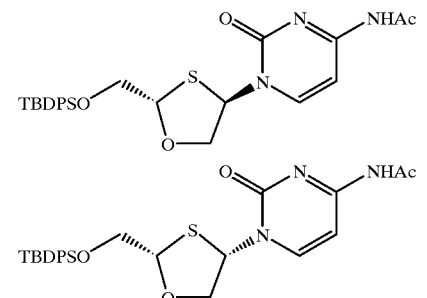

2S-t-BUTYLDIPHENYLSILYLOXYMETHYL-4R-(N-4'-ACETYLCYTOSIN-1'-YL)-1,3-OXATHIOLANE AND
2S-t-BUTYLDIPHENYLSILYLOXYMETHYL-4S-(N-4'-ACETYLCYTOSIN-1'-YL)-1,3-OXATHIOLANE 2,6-lutidine (0.131 ml, 1.13 mmol) and trimethylsilyl trifluoromethanesulfonate (0.218 ml, 1.13 mmol) were added to a suspension of N-4'-acetylcytosine (0.104 g, 0.68 mmol) in dichloroethane (2 ml) at room temperature under argon atmosphere. The mixture was stirred for 15 min and mixture of cis and trans 2S-t-butyldiphenylsiloxymethyl-4-acetoxy-1, 3-oxathiolane (example 18) (0.235 g 0.56 mmol) in dichloroethane (2 ml) and trimethylsilyl trifluoromethanesulfonate (0.109 ml, 1.13 mmol) were introduced successively. The reaction mixture was heated to reflux for half hour and diluted with dichloromethane, washed with saturated aqueous NaHCO$_3$ solution, water, brine, dried over sodium sulfate and concentrated. Chromatography (EtOAc) of the crude product gave a mixture of trans and cis isomer (0.225 g, 78%): $^1$H NMR in CDCl$_3$: δ1.05 (s, 5.4 H), 1.08 (s, 3.6 H), 2.24 (s, 1.2 H), 2.28 (s, 1.8 H), 3.67–4.42 (m, 4 H), 5.26 (t, 0.4 H, J=4.3 Hz), 5.64 (dd, 0.6 H, J=6.8, 4.3 Hz), 6.40 (d, 0.6 H, J=3.8 Hz), 6.53 (d, 0.4 H, J=4.1 Hz), 7.20–7.75 (m, 11 H), 8.00 (d, 0.6 H, J=7.5 Hz), 8.21 (d, 0.4 H, J=7.5 Hz), 9.63 (bs,1 H).

Example 21

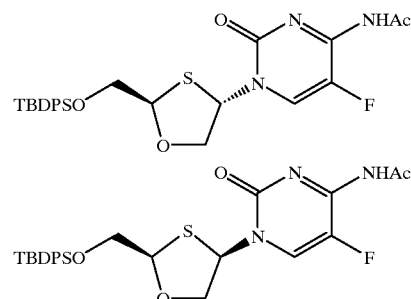

2R-t-BUTYLDIPHENYLSILYLOXYMETHYL-4S-(N-4'-ACETYL-5'-FLUOROCYTOSIN-1'-YL)-1,3-OXATHIOLANE AND
2R-t-BUTYLDIPHENYLSILYLOXYMETHYL-4R-(N-4'-ACETYL-5'-FLUOROCYTOSIN-1'-YL)-1,3-OXATHIOLANE 2,6-lutidine (0.124 ml, 1.07 mmol) and trimethylsilyl trifluoromethanesulfonate (0.207 ml, 1.07 mmol) were added to a suspension of N-4'-acetyl-5'-fluorocytosine (0.110 g, 0.64 mmol) in dichloroethane (3 ml) at room temperature under argon atmosphere. The mixture was stirred for 15 min and mixture of cis and trans 2R-t-butyldiphenylsiloxymethyl-4-acetoxy-1, 3-oxathiolane (example 17) (0.223 g 0.54 mmol) in dichloroethane (3 ml) and trimethylsilyl trifluoromethane-sulfonate (0.103 ml, 0.54 mmol) were introduced successively. The reaction mixture was heated to reflux for half hour and diluted with dichloromethane, washed with saturated aqueous NaHCO$_3$ solution, water, brine, dried over sodium sulfate and concentrated. Chromatography of the crude product gave a mixture of trans and cis isomer which was subjected to preparative TLC separation to give cis isomer (97 mg, 34%) [1 H NMR in CDCl$_3$ δ1.08 (s, 9 H), 2.65 (s, 3 H), 3.90–4.50 (m, 4 H), 5.27 (t, J=4.2 Hz), 6.53 (d, 1 H, J=4.2 Hz), 7.32–7.530 (m, 6 H), 7.55–7.76 (m, 4 H), 8.21 (d, 1 H, J=6.1 Hz)] and trans isomer (68 mg, 24%) [1 H NMR in CDCl$_3$ δ 1.07 (s, 9 H), 2.63 (s, 3 H), 3.56–4.26 (m, 4 H), 5.68 (dd, J=6.9, 4.4 Hz), 6.37 (d, 1 H, J=2.4 Hz), 7.30–7.53 (m, 6 H), 7.57–7.75 (m, 4 H), 7.93 (d, 1 H, J=6.1 Hz)].

Example 22

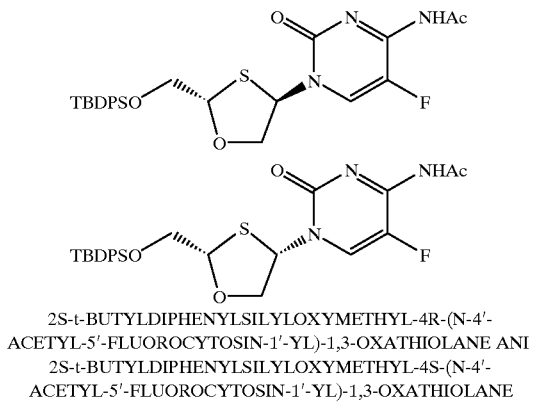

2S-t-BUTYLDIPHENYLSILYLOXYMETHYL-4R-(N-4'-ACETYL-5'-FLUOROCYTOSIN-1'-YL)-1,3-OXATHIOLANE AND
2S-t-BUTYLDIPHENYLSILYLOXYMETHYL-4S-(N-4'-ACETYL-5'-FLUOROCYTOSIN-1'-YL)-1,3-OXATHIOLANE 2,6-lutidine (0.248 ml, 2.13 mmol) and trimethylsilyl trifluoromethanesulfonate (0.418 ml, 2.13 mmol) were added to a suspension of N-4'-acetyl-5'-fluorocytosine (0.218 g, 1.27 mmol) in dichloroethane (4.5 ml) at room temperature under argon atmosphere. The mixture was stirred for 15 min and mixture of cis and trans 2S-t-butyldiphenylsiloxymethyl-4-acetoxy-1,3-oxathiolane (example 18) (0.433 g 1.06 mmol) in dichloroethane (4 ml) and trimethylsilyl trifluoromethane-sulfonate (0.206 ml, 1.06 mmol) were introduced successively. The reaction mixture was heated to reflux for half hour and diluted with dichloromethane, washed with saturated aqueous NaHCO$_3$ solution, water, brine, dried over sodium sulfate and concentrated. Chromatography of the crude product gave a mixture of trans and cis isomer which was subjected to preparative TLC separation to give cis isomer (145 mg, 26%) [$^1$H NMR in CDCl$_3$ δ1.09 (s, 9 H), 2.66 (s, 3 H), 3.90–4.50 (m, 4 H), 5.26 (t, J=4.1 Hz), 6.53 (d, 1 H, J=4.1 Hz), 7.36–7.50 (m, 6 H), 7.55–7.78 (m, 4 H), 8.20 (d, 1 H, J=6.1 Hz)] and trans isomer (119 mg, 21%) [$^1$H NMR in CDCl$_3$ δ1.07 (s, 9 H), 2.64 (s, 3 H), 3.58–4.25 (m, 4 H), 5.68 (dd, J=6.8, 4.2 Hz), 6.37 (d, 1 H, J=2.7 Hz), 7.35–7.51 (m, 6 H), 7.60–7.76 (m, 4 H), 7.93 (d, 1 H, J=6.1 Hz)].

Example 23

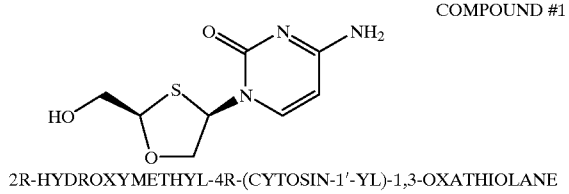

COMPOUND #1

2R-HYDROXYMETHYL-4R-(CYTOSIN-1'-YL)-1,3-OXATHIOLANE

To a solution of 2R-t-butyldiphenylsiloxymethyl-4R-(N-4'-acetylcytosin-1'-yl)-1,3-oxathiolane (example 19) (72 mg, 0.14 mmol) in THF (3 ml) at ambient temperature under an argon atmosphere were slowly added tetrabutylammonium fluoride solution (0.212 ml, 1 M in THF, 0.21 mmol) and glacial acetic acid (0.012 ml, 0.21 mmol). The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated K$_2$CO$_3$ methanol solution and the reaction mixture was stirred at ambient temperature for half an hour. The reaction mixture was neutralized with 1 N HCl/ methanol solution followed by the addition of silica gel (0.5 g). The resulting slurry was subjected to silical gel column chromatography (EtOAc-MeOH, 4:1) to afford the product (27 mg, 91%) as white solid which was triturated in Et$_2$O— MeOH: mp 200° C. (dec.); [α]D$^{25}$ -126.8° (c, 0.5, MeOH); $^1$H NMR (DMSO-d$_6$): δ3.70–3.82 (m, 2 H), 3.91 (dd,1 H, J=10.4, 4.6 Hz), 4.38 (d, 1 H, J=10.4 Hz), 5.16 (t, 1 H, J=4.6 Hz), 5.32 (t, 1 H, J=5.8 Hz), 5.75 (d, 1 H, J=7.4 Hz), 6.32 (d,1 H, J=4.6 Hz), 7.12 (bs, 1 H), 7.23 (bs, 1 H), 7.84 (d,1 H, J=7.4 Hz); $^{13}$C NMR (DMSO-d$_6$): δ62.7, 63.1, 77.4, 89.0, 95.6, 142.4, 155.4, 165.8.

In order to assess the enantiomeric purity of the synthesized end nucleoside product or to resolve the racemic mixture of deprotected nucleoside analogues chiral HPLC methods were used. For example, the compound #1 above, was found to have a retention time of 43.88 min under the following conditions:

| Type of column: | cyclobond RSP 4.6 × 250 nm |
|---|---|
| Flow rate: | 0.27 ml/min |
| Solvent: | 0.05% TFAA, PH 7.0 |
| Detection: | 254 nm |

Example 24

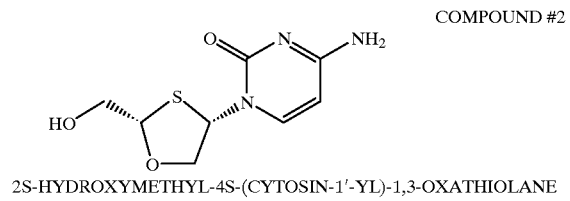

COMPOUND #2

2S-HYDROXYMETHYL-4S-(CYTOSIN-1'-YL)-1,3-OXATHIOLANE

To a solution of 2S-t-butyldiphenylsiloxymethyl-4S-(N-4'-acetylcytosin-1'-yl)-1,3-oxathiolane (example 20) (202 mg, 0.40 mmol) in THF (3.5 ml) at ambient temperature under an argon atmosphere were slowly added tetrabutylammonium fluoride solution (0.595 ml, 1 M in THF, 0.60 mmol) and glacial acetic acid (0.034 ml, 0.60 mmol). The reaction mixture was allowed to stir for 1 h, followed by the addition of silica gel (0.9 g). The resulting slurry was subjected to silical gel column chromatography (EtOAc-MeOH, 9:1) to give the desilylated product. The desilylated product was dissolved in saturated K$_2$CO$_3$ methanol solution and the reaction mixture was stirred at ambient temperature for half an hour. The reaction mixture was neutralized with 1 N HCl methanol solution followed by the addition of silica gel (0.9 g). The resulting slurry was subjected to silical gel column chromatography (EtOAc-MeOH, 4:1) to afford the product (74 mg, 81%) as white solid which was triturated in Et$_2$O—MeOH: mp 220° C. (dec.); [α]D$^{25}$ +118.6° (c, 0.5, MeOH); $^1$H NMR (DMSO-d$_6$): δ3.70–3.82 (m, 2 H), 3.92 (dd,1 H, J=10.6, 4.6 Hz), 4.38 (d, 1 H, J=10.6 Hz), 5.17 (t, 1 H, J=4.5 Hz), 5.32 (t, 1 H, J=5.8 Hz), 5.75 (d, 1 H, J=7.4 Hz), 6.32 (d,1 H, J=4.6 Hz), 7.12 (bs, 1 H), 7.22 (bs, 1 H), 7.85 (d,1 H, J=7.4 Hz); $^{13}$C NMR (DMSO-d$_6$): δ63.0, 63.1, 77.4, 88.9, 95.1, 142.4, 155.4, 165.7.

In order to assess the enantiomeric purity of the synthesized end nucleoside product or to resolve the racemic mixture of deprotected nucleoside analogues chiral HPLC methods were used. For example, the compound #2 above, was found to have a retention time of 48.18 min under the following conditions:

| Type of column: | cyclobond RSP 4.6 × 250 nm |
|---|---|
| Flow rate: | 0.27 ml/min |
| Solvent: | 0.05% TFAA, PH 7.0 |
| Detection: | 254 nm |

Example 25

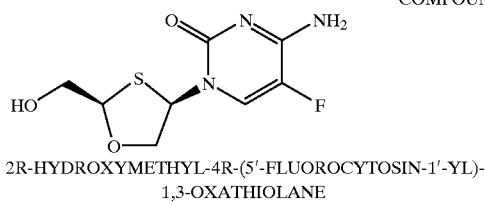

COMPOUND #3

2R-HYDROXYMETHYL-4R-(5'-FLUOROCYTOSIN-1'-YL)-1,3-OXATHIOLANE

To a solution of 2R-t-butyldiphenylsiloxymethyl-4R-(N-4'-acetyl-5'-fluorocytosin-1'-yl)-1,3-oxathiolane (example 21) (152 mg, 0.29 mmol) in THF (3.5 ml) at ambient temperature under an argon atmosphere were slowly added tetrabutylammonium fluoride solution (0.432 ml, 1 M in THF, 0.43 mmol) and glacial acetic acid (0.025 ml, 0.43 mmol). The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated $K_2CO_3$ methanol solution and the reaction mixture was stirred at ambient temperature for half an hour. The reaction mixture was neutralized with 1 N HCl methanol solution followed by the addition of silica gel (0.5 g). The resulting slurry was subjected to silical gel column chromatography (EtOAc-MeOH, 4:1) to afford the product (58 mg, 81%) as white solid which was triturated in $Et_2O$—MeOH: mp 183° C. (dec.); $[\alpha]D^{25}$ −86.5° (c, 0.57, MeOH); $^1$H NMR (DMSO-$d_6$): δ3.70–4.50 (m, 4 H), 5.18 (t, 1 H, J=3.6 Hz), 5.44 (t, 1 H, J=5.8 Hz), 6.25–6.30 (m,1 H), 7.56 (bs, 1 H), 7.80 (bs, 1 H), 8.14 (d,1 H, J=7.2 Hz); $^{13}$C NMR (DMSO-$d_6$): δ62.2, 63.4, 77.5, 88.9, 126.7, 127.1, 134.7, 137.9, 153.8, 157.5, 157.7.

In order to assess the enantiomeric purity of the synthesized end nucleoside product or to resolve the racemic mixture of deprotected nucleoside analogues chiral HPLC methods were used. For example, the compound #3 above, was found to have a retention time of 16.73 min under the following conditions:

| Type of column: | cyclobond RSP 4.6 × 250 nm |
|---|---|
| Flow rate: | 0.43 ml/min |
| Solvent: | 0.05% TFAA, PH 7.0 |
| Detection: | 254 nm |

Example 26

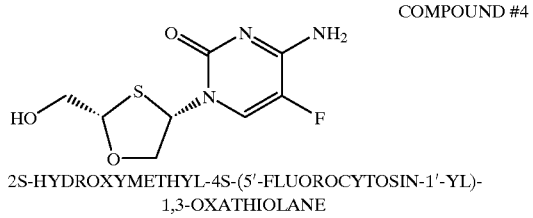

COMPOUND #4

2S-HYDROXYMETHYL-4S-(5'-FLUOROCYTOSIN-1'-YL)-1,3-OXATHIOLANE

To a solution of 2S-t-butyldiphenylsiloxymethyl-4S-(N-4'-acetyl-5'-fluorocytosin-1 '-yl)-1,3-oxathiolane (example 22) (78 mg, 0.15 mmol) in THF (3 ml) at ambient temperature under an argon atmosphere were slowly added tetrabutylammonium fluoride solution (0.222 ml, 1 M in THF, 0.22 mmol) and glacial acetic acid (0.013 ml, 0.22 mmol. The reaction mixture was allowed to stir for 1 h, followed by the addition of silica gel (0.5 g). The resulting slurry was subjected to silical gel column chromatography (EtOAc-MeOH, 9:1) to give the desilylated product. The desilylated product was dissolved in saturated $K_2CO_3$ methanol solution and the reaction mixture was stirred at ambient temperature for half hour. The reaction mixture was neutralized with 1 N HCl methanol solution followed by the addition of silica gel (0.5 g). The resulting slurry was subjected to silical gel column chromatography (EtOAc-MeOH, 4:1) to afford the product (36 mg, 98%) as white solid which was triturated in $Et_2O$—MeOH: mp 180° C. (dec.); $[\alpha]D^{25}$ +75.7° (c, 0.56, MeOH); $^1$H NMR (DMSO-$d_6$): δ3.69–4.50 (m, 4 H), 5.18 (t, 1 H, J=3.7 Hz), 5.44 (t, 1 H, J=5.8 Hz), 6.25–6.29 (m,1 H), 7.55 (bs, 1 H), 7.8 (bs, 1 H), 8.14 (d,1 H, J=7.2 Hz); $^{13}$C NMR (DMSO-$d_6$): 61.8, 63.1, 77.1, 88.6, 126.3, 126.8, 134.4, 137.6, 153.5, 157.1, 157.3.

In order to assess the enantiomeric purity of the synthesized end nucleoside product or to resolve the racemic mixture of deprotected nucleoside analogues chiral HPLC methods were used. For example, the compound #4 above, was found to have a retention time of 15.07 min under the following conditions:

| Type of column: | cyclobond RSP 4.6 × 250 nm |
|---|---|
| Flow rate: | 0.43 ml/min |
| Solvent: | 0.05% TFAA, PH 7.0 |
| Detection: | 254 nm |

Example 27

ANTIVIRAL ACTIVITY:

FORMAZAN ASSAY ON MT-4 AND 3TC™—RESISTANT CELL LINES

Anti-HIV-1 antiviral activity was determined in MT-4 cells and MT-4 cells that have been made resistant to 3TC™. A suspension of cells (approximately $10^6$ cells/ml) in RPMI 1640 growth medium was infected with HIV-1 strain RF at a M.O.I. of $10^{-3}$ infectious units/cell. An uninfected cell suspension was prepared in parallel to evaluate drug-induced cytotoxicity. The two suspensions were incubated for 90 minutes at room temperature. Test compounds were serially diluted in 10-fold decrements from 100 μg/ml to 0.01 μg/ml (final concentrations in two 96 well microtitre plates. 20 μl of infected cell suspension were inoculated into each well of one of the plates (anti-viral), while 20 μl of uninfected cell suspension were added to each well of the second plate (cytotoxicity). The plates were then incubated for 7 days at 37° C. After incubation, 10 μl of 3-(4,5-dimethylthiazol-2-yl)-2,5-diphenyltetrazolium bromide (MTT) at 20 mg/ml was added to all wells and the plates incubated for a further 90 minutes at 37° C.

150 μl of 10% (v/v) alcoholic Triton X-100 was then added and the cells resuspended. After 15 minutes at room temperature, the plates were analyzed in a Multiskan MC reader at 405 nm. Conversion of yellow MMT to its formazan derivative is maximum in uninfected cells, and absent in untreated infected cells. The optical density values for the cytotoxicity controls and the antiviral test wells were graphically plotted and the dose of compounds required to inhibit the conversion of MMT to 50% of the untreated uninfected controls was calculated. In this way, both the 50% cytotoxic dose (CD 50%) and the 50% anti-viral dose (ID 50%) can be calculated. Table 1 shows CD 50% and ID 50% values obtained for:

TABLE 1

(MT-4 assay)

| COMPOUND | $ID_{50}$ (μg/ml) | $CD_{50}$ (μg/ml) |
|---|---|---|
| BCH-270 (example 7) | 4.0 | >100 |
| #1 (example 23) | 13 | >100 |
| #2 (example 24) | 4.4 | >100 |
| #3 (example 25) | 6.0 | >100 |
| #4 (example 26) | 2.9 | 100 |
| AZT (reference) | 0.01 | >1 |

TABLE 2

3TC-RESISTANT CELLS ($Met^{184}$ → Ile mutation)

| COMPOUND | $ID_{50}$ (μg/ml) | $CD_{50}$ (μg/ml) |
|---|---|---|
| #1 (example 23) | 8.5 | >100 |
| #2 (example 24) | 42 | >100 |
| #3 (example 25) | 3.4 | >100 |
| #4 (example 26) | 3.0 | 100 |
| 3TC ™ | >100 | >100 |

INHIBITION OF SYNCYTIUM FORMATION

C8166 cells were infected with HIV-1 (strain RF) at a moil of $1 \times 10^{-3}$ infectious units/cell and adsorbed at room temperature for 60 minutes. After adsorption, the cells were washed three times in growth medium. Aliquots of $10^5$ cells were added to each well of 24-well plates containing serial dilution of test compounds at final concentrations of 50 μg/ml to 0.05μg/ml in RPMI® 1640 growth medium. Untreated infected cells and untreated uninfected cells were also included as controls. The plates were incubated at 37° C./5% $CO_2$ for 3–4 days in humidified containers. The cells were examined daily for evidence of HIV-1 induced syncytium formation. The syncytia were quantified by reference to the untreated infected controls, and the dose of compound required to reduce the cytopathic effect by 50% ($ID_{50}$) was calculated.

TABLE 3

(SYNCYTIUM FORMATION)

| COMPOUND | $ID_{50}$ (μg/ml) | $CD_{50}$ (μg/ml) |
|---|---|---|
| #2 (example 25) | 0.08 | >100 |
| #3 (example 25) | 0.17 | >100 |
| #4 (example 26) | 0.03 | >100 |

CBM ASSAY

Assays on cord blood mononuclear cells were done substantially as described in Gu et al., J. Virol. (1992), 66:7128–7135.

In short, viruses ($HTLV-III_B$) that had initially been grown on MT-4 cells were passaged onto phytohemaglutinin-prestimulated cord blood mononuclear cells (CBM). For subsequent analysis, samples of CBM ($5 \times 10^5$ cells per mL) were pretreated with various concentrations of the different compounds for 4 h and were then inoculated with CBL-grown HIV-1 at a multiplicity of infection of 1.0 in the concentration of the compound used for the pretreatment. Fresh medium, including the appropriate concentration of the compound was added three times weekly, and fresh phytohemaglutinin-prestimulated CBM ($5 \times 10^5$ cells per mL) were added at 2-day intervals. The calculation of $IC_{50}$ was determined on the basis of RT levels in culture fluids as described in Gao et al., (1992), J. Virol. 66: 12–19.

TABLE 4

(CBM)

| COMPOUND | $ID_{50}$ (μg/ml) | $CD_{50}$ (μg/ml) |
|---|---|---|
| BCH-270 (example 7) | 0.03 | >23 |
| #1 (example 23) | 0.05–1.22 | >23 |
| #2 (example 24) | 0.03–1.22 | >23 |
| #3 (example 25) | 0.002–0.05 | >23 |
| #4 (example 26) | 0.02–0.05 | >23 |
| AZT (reference) | <0.002 | >1 |

DETERMINATION OF IC50 (μM) IN DIFFERENT MUTATED ISOLATES OF HIV-1 IN THE PRESENCE OF DIFFERENT ANTIVIRAL COMPOUNDS

The procedure is similar to the procedure used in the CBM assay, with the exception that constructed virus and construted mutated virus were used.

The constructed virus HXB2D-65 correspond to the ddC resistance mutation and the constructed virus HXB2D-184 correspond to the 3TC™ and FTC resistance mutation.

TABLE 5

Values of $IC^{50}$ in CBMCs with Differents Mutated Isolates of HIV-1

| COMPOUNDS | $III_B$ | HXB2D | HXB2D-65 K → R | HXB2D-184 M → V |
|---|---|---|---|---|
| #1 | 0.22 | 1.0 | 2.5 | 0.53 |
| #2 | 0.28 | 0.1 | 3.5 | 3.0 |
| #3 | 0.83 | 3.0 | 11.5 | 9.0 |
| #4 | 0.34 | 3.0 | 6.5 | 2.0 |
| AZT | 0.002 | 0.002 | 0.001 | 0.001 |
| 3TC ™ | 0.01 | 0.08 | 0.125 | 42.5 |

DETERMINATION OF IC50 (μM) IN HIV-1 ACUTELY INFECTED CELL LINES IN THE PRESENCE OF DIFFERENT ANTIVIRAL COMPOUNDS

Various cell lines were infected with HTLV-IIIb (TCID50=200) and then cultured with various concentrations of drug. IC50 was determined by measuring p24 antigen levels in the supernatant of cultures at day 6 of infection.

TABLE 6

| COMPOUND | ID$_{50}$ (μg/ml) | | | | |
|---|---|---|---|---|---|
| | MT-4 | Jurkat | H9 | U937 | CEM |
| #1 (example 23) | 2.8 | 3.0 | 0.3 | 0.4 | 0.2 |
| #2 (example 24) | 0.9 | 1.8 | 0.075 | 0.3 | 0.4 |
| #3 (example 25) | 3.0 | 3.5 | 0.1 | 0.6 | 0.2 |
| #4 (example 26) | 3.2 | 6.0 | 1.0 | 0.4 | 0.3 |
| AZT (reference) | 0.005 | 0.01 | 0.07 | 0.04 | 0.01 |

EVALUATION OF CELL CULTURE INHIBITORY DOSE (CCID50)

Cell growth was determined by cell counting and viability by trypan blue exclusion 7 days post drug treatment. CCID50 is expressed as the drug concentration which inhibits 50% of cell growth.

TABLE 7

| COMPOUNDS | (CCID50 in Different Cells (μM)) | | | | | |
|---|---|---|---|---|---|---|
| | CBMCs | MT-4 | U937 | Jurkat | H9 | CEM |
| #1 (example 23) | >500 | >500 | >500 | 450 | >500 | >500 |
| #2 (example 24) | 105 | >500 | 22 | 11 | >500 | 103 |
| #3 (example 25) | >500 | >500 | >500 | >500 | >500 | >500 |
| #4 (example 26) | >500 | >500 | >500 | >500 | >500 | >500 |
| AZT | 45 | 110 | 110 | >500 | 200 | 500 |

INHIBITION OF HEPATITIS B VIRUS.

The method used for this test is described in detail in Korba et al., Antiviral Research 15, 217–228 (1992) which is shortly described as follows:

Hep G2 cells transfected with human hepatitis B virus genomic DNA (2.2.15 cells) were grown and maintained in RPMI-1640 culture medium containing 5 foetal bovine serum, 2 mM glutamine and 50 μg/ml gentamicin sulphate, and checked routinely for G418 resistance. Cultures of 2.2.15 cells were grown to confluence in 24 well tissue culture plates and maintained for 2 to 3 days in that condition prior to drug treatment.

Drugs were dissolved in sterile water or sterile 50% DMSO in water at concentrations 100-fold higher than the higher test concentration. These solutions were diluted as needed in culture medium.

The culture medium on the confluent cells was changed 24 hours prior to exposure to test compounds. During the 10 day treatment, the culture medium was changed daily. After 10 days of the treatment, the culture medium was collected and frozen at −70° C. for HBV DNA analysis.

To analyze extracellular HBV DNA, 0.2 ml samples of culture medium were incubated for 20 minutes at 25° C. in 1 M NaOH/10X SSC (1X SSC is 0.15 M NaCl/ 0.015 M Sodium Citrate, pH 7.2) and then applied to nitrocellulose membranes presoaked in 20X SSC. Filters were then rinsed in 2X SSC and baked at 80° C. for 1 hour under vacuum.

A purified 3.2 kb EcoR1 HBV DNA fragment was labeled with [$^{32}$P]dCTP by nick translation and used as a probe to detect HBV DNA on the dot-blot by DNA hybridization. After washing, the hybridized blot was dried and $^{32}$P was quantified using an Ambis beta scanner.

TABLE 8

| | (HBV) | |
|---|---|---|
| COMPOUND | ID$_{50}$ (μg/ml) | CD$_{50}$ (μg/ml) |
| BCH-270 (example 7) | 7.5 | >10 |
| Compound #2 (example 24) | 4 | >10 |

What is claimed is:

1. A method of treating 3TC™-resistant or FTC-resistant human immunodeficiency virus infections in mammals comprising the step of administering to said mammal a pharmaceutical formulation, the pharmaceutical formulation comprising a compound selected from the group consisting of
   a. 2R-hydroxymethyl-4R-(cytosin-1'-yl)-1,3-oxathiolane;
   b. 2S-hydroxymethyl-4S-(cytosin-1'-yl)-1,3-oxathiolane;
   c. 2R-hydroxymethyl-4R-(5'-fluorocytosin-1'-yl)-1,3-oxathiolane;
   d. 2S-hydroxymethyl-4S-(5'-fluorocytosin-1'-yl)-1,3-oxathiolane; and
   e. pharmaceutically acceptable salts and esters of the foregoing compounds in an amount effective for treating 3TC™-resistant or FTC-resistant human immunodeficiency virus infections, wherein 3TC™ is 2R-hydroxmethyl-5S-(cytosin-1'-yl)-1,3-oxathiolane and FTC is 2-hydroxymethyl-5-(5'-fluorocytosin-1'-yl)-1,3-oxathiolane, the pharmaceutical formulation further comprising a pharmaceutically acceptable carrier.

2. The method according to claim 1, wherein said mammal is a human.

3. A method according to claim 1, wherein said compound is 2R-hydroxymethyl-4R-(cytosin-1'-yl)-1,3-oxathiolane, a pharmaceutically acceptable salt thereof or a pharmaceutically acceptable ester thereof.

4. A method according to claim 1, wherein said compound is 2S-hydroxymethyl-4S-(cytosin-1')-1,3-oxathiolane, a pharmaceutically acceptable salt thereof or a pharmaceutically acceptable ester thereof.

5. A method according to claim 1, wherein said compound is 2R-hydroxymethyl-4R-(5'-fluorocytosin-1'-yl)-1,3-oxathiolane, a pharmaceutically acceptable salt thereof or a pharmaceutically acceptable ester thereof.

6. A method according to claim 1, wherein said compound is 2S-hydroxymethyl-4S-(5'-fluorocytosin-1'-yl)-1,3-oxathiolane, a pharmaceutically acceptable salt thereof or a pharmaceutically acceptable ester thereof.

7. A method according to claim 1, wherein said compound is administered to said mammal in an amount 3–120 mg per kilogram of body weight per day.

8. A method according to claim 1, wherein said compound is administered to said mammal in an amount 6–90 mg/kg/day.

9. A method according to claim 1, wherein said compound is administered to said mammal in an amount 15–60 mg/kg/day.

10. A method according to claim 1, wherein said pharmaceutical formulation contains 120–1000 mg of said compound.

11. A method according to claim 1, wherein said pharmaceutical formulation is administered by intravenous injection.

12. A method recording to claim 1, wherein
said pharmaceutically acceptable salts are selected from the group consisting of alkali metal salts, alkaline earth metal salts, ammonium salts, N-$(C_{1-4}$-alkyl$)_4^+$salts and salts derived from hydrochloric acid, hydrobromic acid, sulfuric acid, nitric acid, perchloric acid, fumaric acid, maleic acid, phosphoric acid, glycollic acid, lactic acid, salicylic acid, succinic acid, p-toluene sulfonic acid, tartaric acid, acetic acid, citric acid, methanesulfonic acid, formic acid, benzoic acid, malonic acid, napthalene-2-sulfonic acid, and benzenesulfonic acid; and
wherein said pharmaceutically acceptable esters are selected from the group consisting of methyl, ethyl, n-propyl, t-butyl, n-butyl, methoxymethyl, benzyl, phenoxymethyl, phenyl, N-methyldihydropyrindyl, methanesulfonyl, sulfate, L-valyl, L-isoleucyl, monophosphate, diphosphat and triphosphate esters.

13. A method according to claim 3, wherein said compound is 2R-hydroxymethyl4R-(cytosin-1'-yl)1,3-oxathiolane.

14. A method according to claim 4, wherein said compound is 2S-hydroxymethyl4S-(cytosin-1'-yl)1,3-oxathiolane.

15. A method according to claim 5, wherein said compound is 2R-hydroxymethyl-4R-(5'-fluorocytosin-1'-yL)-1,3-oxathiolane.

16. A method according to claim 6 , wherein said compound is 2S-hydroxymethyl-4S-(5'-fluorocytosin-1'-yL)-1,3-oxathiolane.

17. A method according to claim 1, wherein said pharmaceutical formulation contains 10–1500 mg per unit dosage of said compound.

18. A method according to claim 17, wherein said pharmaceutical formulation contains 20–1000 mg per unit dosage of said compound.

19. A method according to claim 18, wherein said pharmaceutical formulation contains 50 to 700 mg per unit dosage of said compound.

20. A method according to claim 1, wherein said pharmaceutical formulation is administered at a dose of 1–750 mg/kg/day.

* * * * *

UNITED STATES PATENT AND TRADEMARK OFFICE
CERTIFICATE OF CORRECTION

PATENT NO. : 6,228,860 B1
DATED : May 8, 2001
INVENTOR(S) : Mansour et al.

It is certified that error appears in the above-identified patent and that said Letters Patent is hereby corrected as shown below:

Title page,
Item [63], delete "which is a continuation-in-part of application No. 07/791,441, filed on Nov. 13, 1991, now abandoned, which is a continuation-in-part of application No. 07/612,840, filed on Nov. 13, 1990, now abandoned".

Column 1,
Lines 7-10, delete "which is a continuation-in-part of application No. 07/791,441, now abandoned, which is a continuation-in-part of application Ser. No. 07/612,840, now abandoned".

Column 36,
Lines 6 and 9, delete "yL" and insert -- yl --.

Signed and Sealed this

Twenty-fifth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,228,860 B1
DATED : May 8, 2001
INVENTOR(S) : Mansour et al.

It is certified that error appears in the above-identified patent and that said Letters Patent is hereby corrected as shown below:

<u>Title page,</u>
Item [63], delete "which is a continuation-in-part of application No. 07/791,441, filed on Nov. 13, 1991, now abandoned, which is a continuation-in-part of application No. 07/612,840, filed on Nov. 13, 1990, now abandoned."

<u>Column 1,</u>
Lines 7-10, delete "which is a continuation-in-part of application No. 07/791,441, now abandoned, which is a continuation-in-part of application Ser. No. 07/612,840, now abandoned."

Signed and Sealed this

Tenth Day of June, 2003

JAMES E. ROGAN
*Director of the United States Patent and Trademark Office*